(12) United States Patent
Foley et al.

(10) Patent No.: US 8,779,198 B2
(45) Date of Patent: Jul. 15, 2014

(54) RING OPENING OF LACTONES AND LACTAMS

(75) Inventors: Megan Alene Foley, Somerville, MA (US); Timothy F. Jamison, Somerville, MA (US); Oljan Repic, Randolph, NJ (US)

(73) Assignees: Novartis AG, Basel (CH); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/389,849

(22) PCT Filed: Aug. 11, 2010

(86) PCT No.: PCT/US2010/045121
§ 371 (c)(1),
(2), (4) Date: Mar. 9, 2012

(87) PCT Pub. No.: WO2011/019789
PCT Pub. Date: Feb. 17, 2011

(65) Prior Publication Data
US 2012/0165555 A1   Jun. 28, 2012

Related U.S. Application Data

(60) Provisional application No. 61/232,886, filed on Aug. 11, 2009, provisional application No. 61/232,880, filed on Aug. 11, 2009.

(51) Int. Cl.
*C07C 231/02* (2006.01)

(52) U.S. Cl.
CPC .................................. *C07C 231/02* (2013.01)
USPC ........................................................ 564/157

(58) Field of Classification Search
CPC ..................................................... C07C 231/02
USPC .......................................................... 564/157
See application file for complete search history.

(56) References Cited

FOREIGN PATENT DOCUMENTS

| EP | 0678503 | 10/1995 |
|----|---------|---------|
| WO | WO 03/103653 | 12/2003 |
| WO | WO 2005/051895 | 6/2005 |
| WO | WO 2006/131304 | 12/2006 |
| WO | WO 2007/045420 | 4/2007 |

OTHER PUBLICATIONS

Liu et al. (Tetrahedron Letters 42 (2001) 2439-2441).*
Dong et al. (Tetrahedron Letters 46 (2005) 6337-6340).*

* cited by examiner

*Primary Examiner* — Robert Havlin
(74) *Attorney, Agent, or Firm* — Ann R. Pokalsky, Esq.; Dilworth & Barrese, LLP

(57) ABSTRACT

The present invention provides a novel process for opening a lactone and/or a lactam ring. More particularly, the present invention provides a process that employs a novel catalyst in the opening of a lactone ring and/or a lactam ring. Additionally, the present invention also provides a novel deprotection process of any protecting group present in either the lactone ring-containing and/or lactam ring-containing compound and/or in the ring-opened product thereof.

9 Claims, 5 Drawing Sheets

Graph 1: Lactone Opening with No Solvent 120°C

Graph 2: Lactone Opening with No Solvent 120°C

Graph 3: Varying Equiv. of 2-Ethylhexanoic Acid

* with 7 equiv. acid decomposition of product observed at 120 °C

Graph 4: Effect of Temperature on the Lactone Opening Reaction

*Decomposition of product observed

Graph 5: Effect of Solvent on the Lactone Opening Reaction

Graph 6: Removal of the *tert*-butyloxycarbonyl group (Boc)

RING OPENING OF LACTONES AND LACTAMS

This application is a National Phase application of PCT/US2010/045121, filed Aug. 11, 2010, which claims benefit of Provisional Application No. 61/232,886, filed Aug. 11, 2009 and Provisional Application No. 61/232,880, filed Aug. 11, 2009, which in their entirety are incorporated herein by reference.

The present invention provides a novel process for opening a lactone and/or a lactam ring. More particularly, the present invention provides a process that employs a novel catalyst in the opening of a lactone ring and/or a lactam ring.

Additionally, the present invention also involves the opening of a lactone and/or a lactam ring, either by the above-described novel catalyst, or by another catalyst, followed by a novel deprotection process of any protecting group present in either the lactone ring-containing and/or lactam ring-containing compound and/or in the ring-opened product thereof.

Some synthesis processes for forming various renin inhibitors, or pharmaceutically acceptable salts thereof, utilize a ring-opening step of a lactone-containing and/or lactam-containing compound.

Therefore, the present invention is also directed to processes for the preparation of these renin inhibitors and pharmaceutical salts thereof, as well as their intermediates, by employing the novel catalyst in ring-opening of a lactone-containing and/or lactam-containing compound optionally followed by converting any of said intermediates, renin inhibitors, or their pharmaceutical salts thereof, by the use of a novel process to the desired renin inhibitor.

Additionally, the present invention is also directed to processes for the preparation of these renin inhibitors and pharmaceutical salts thereof, as well as their intermediates, by employing another catalyst in ring-opening of a lactone-containing and/or lactam-containing compound followed deprotecting any of said intermediates, renin inhibitors, or their pharmaceutical salts thereof, by the use of a novel process to obtain the desired renin inhibitor.

BACKGROUND OF THE INVENTION

The use of lactone ring-containing and/or lactam ring-containing compounds have wide utility in various industrial and commercial applications, e.g., pharmaceuticals. The desire to quickly and efficiently open lactone-ring containing and/or lactam ring-containing compounds lies in the desire to improve the availability of such opened compounds in any application that requires the use of such compounds as desired components. Additionally, the deprotection of any protecting groups present on a lactone ring-containing and/or lactam ring-containing compound and/or its opened product may in certain instances be desirable from a commercial standpoint.

The use of such compounds as intermediates in the production of renin-inhibitors is a particularly commercially important application.

Renin passes from the kidneys into the blood where it affects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

Various renin inhibitor compounds can interfere with the renin-angiotensin system at the beginning of angiotensin II biosynthesis. Processes for making such renin inhibitor compounds can be timely and costly from a commercial standpoint. There is a continual desire for improvements in processes of making various renin inhibitor compounds, and their useful intermediates, that will reduce time, cost, and improve the efficiency of obtaining pharmaceuticals obtained therefrom.

SUMMARY OF THE INVENTION

It has been surprisingly found that lactone-ring containing and/or lactam ring-containing compounds can have their lactone ring and/or lactam ring effectively opened in an expeditious and less costly manner by using specific acid catalysts.

Further, it has been surprisingly found that the use of such novel catalysts can optionally be used in ranges comprising an equimolar amount of such catalyst to the lactone-ring containing and/or lactam ring-containing compound. In some embodiments, a process for opening the ring of a ring-containing compound which comprises reacting a ring-containing compound possessing at least one lactone ring and/or at least one lactam ring with at least one amine in the presence of at least one carboxylic acid under conditions sufficient to open the at least one ring and provide ring-opened reaction product is provided. In certain embodiments, a process for opening the ring of a ring-containing compound which comprises reacting a ring-containing compound possessing at least one lactone ring and/or at least one lactam ring with at least one amine in the presence of a catalytically effective amount of at least one carboxylic acid (e.g., a carboxylic acid catalyst) under conditions sufficient to open the at least one ring and provide ring-opened reaction product is provided. A catalytically effective amount of the carboxylic acid may be an amount of carboxylic acid that assists in opening a lactone and/or lactam ring without being substantially consumed and/or consumed.

Still further, it has been surprisingly found that compounds containing protecting groups, such as for example, lactone-ring containing and/or lactam ring-containing compounds having protecting groups, the ring-opened products thereof, such as, for example, renin inhibitor compounds, or their pharmaceutically acceptable salts thereof, can be successfully deprotected by the use of aqueous halogenic acids, instead of solid and/or gaseous forms of the same, whether such lactone-ring containing and/or lactam ring containing compounds are opened using the novel catalyst or not, or further, regardless of whether or not such compounds containing protecting groups contain lactone and/or lactam ring(s).

It has been surprisingly found that intermediates (such as lactone ring-containing compound and/or lactam ring containing compound and/or their ring-opened products) used in the production of renin inhibitors, such as aliskiren (2S,4S, 5S,7S)—N-(3-amino-2,2-dimethyl-3-oxopropyl)-2,7-di(1-methylethyl)-4-hydroxy-5-amino-8-[4-methoxy-3-(3-methoxy-propoxy)phenyl]octanamide hemifumarate), can be made in an expeditious and less costly manner with the use of specific acid catalysts, as can the renin inhibitors themselves, or pharmaceutically acceptable or unacceptable salts thereof.

Further, the use of such novel catalysts can optionally be used in ranges comprising an equimolar amount of such catalyst to the lactone-ring containing and/or lactam ring-containing compound. It has also been surprisingly found that renin-inhibitor compounds, intermediates thereof (lactone ring-containing compound and/or lactam ring-containing compound, or opened versions thereof), or pharmaceutically acceptable salts thereof, any one of which contain protecting groups, can be successfully deprotected by the use of aqueous halogenic acids, instead of solid and/or gaseous forms of the same, whether such lactone-ring containing and/or lactam ring containing compounds are opened using the novel catalyst or not.

There is provided herein a lactone and/or lactam ring-opening process comprising reacting at least one compound comprising at least one lactone ring and/or at least one lactam ring with at least one amine in the presence of at least one carboxylic acid (e.g., monocarboxylic acid, dicarboxylic acid) under conditions sufficient to provide for the opening of the lactone ring and/or lactam ring.

There is provided herein a lactone and/or lactam ring-opening process comprising reacting at least one compound comprising at least one lactone ring and/or at least one lactam ring with at least one amine in the presence of at least one catalyst (e.g., a carboxylic acid present in a catalytically effective amount) and removing at least one protecting group present on the ring-opened reaction product with aqueous halogenic acid.

It will be understood herein that the "removing at least one protecting group present on the ring-opened reaction product with aqueous halogenic acid" can comprise removing at least one protecting group present on the compound comprising at least one lactone ring and/or at least one lactam ring prior to reaction with amine and/or or removing at least one protecting group on the ring-opened reaction product following the reaction with amine.

There is also provided herein a process for making δ-amino-γ-hydroxy-ω-aryl-alkanoic acid amide of the general formula (I):

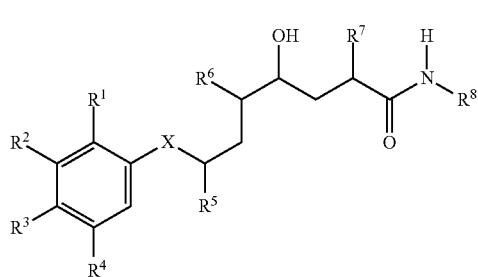

(I)

wherein $R^1$ is hydrogen, hydroxy, lower alkoxy, cycloalkoxy, lower alkoxy-lower alkoxy or free or esterified or amidated carboxy-lower alkoxy, $R^2$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, optionally hydrogenated heteroaryl-lower alkoxy, cyano-lower alkoxy, free or esterified or amidated carboxy-lower alkoxy or free or esterified or amidated carboxy-lower alkyl, $R^3$ is optionally halogenated lower alkyl, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene; cyano-lower alkoxy or free or esterified or amidated carboxy lower alkoxy, or together with $R^4$ is lower alkylenedioxy or a fused-on benzo or cyclohexeno ring, $R^4$ together with $R^3$ is lower alkylenedioxy or a fused-on benzo or cyclohexeno ring, or is hydrogen, lower alkyl, hydroxy, lower alkoxy or cycloalkoxy, X is methylene or hydroxymethylene, $R^5$ is lower alkyl or cycloalkyl, $R^6$ is unsubstituted or N-mono- or N,N-di-lower alkylated or N-lower alkanoylated amino, $R^7$ is hydrogen, lower alkyl, lower alkenyl, cycloalkyl or aryl-lower alkyl, and $R^8$ is lower alkyl, cycloalkyl, free or aliphatically esterified or etherified hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterideal or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, and to the salts thereof, comprising:

reacting an intermediate compound to said δ-amino-γ-hydroxy-ω-aryl-alkanoic acid amide, wherein the intermediate compound comprises at least one lactone ring and/or at least one lactam ring, with at least one amine in the presence of at least one carboxylic acid under conditions sufficient to provide for the opening of the lactone ring and/or lactam ring to provide δ-amino-γ-hydroxy-ω-aryl-alkanoic acid amide, or, converting said ring-opened reaction product to provide δ-amino-γ-hydroxy-ω-aryl-alkanoic acid amide.

In a further embodiment herein there is provided a process of making a δ-amino-γ-hydroxy-ω-aryl-alkanoic acid amide of the general formula (I), which comprises:

reacting an intermediate compound to said δ-amino-γ-hydroxy-ω-aryl-alkanoic acid amide, wherein the intermediate compound comprises at least one lactone ring and/or at least one lactam ring, with at least one amine in the presence of at least one catalyst under conditions sufficient to provide for the opening of the lactone ring and/or lactam ring; and, removing at least one protecting group on the intermediate compound and/or removing at least one protecting group on the ring-opened reaction product, with aqueous halogenic acid.

Similar to as stated above, it will be understood herein that the "removing at least one protecting group present on the intermediate compound and/or removing at least one protecting group on the ring-opened reaction product, with aqueous halogenic acid" can comprise removing at least one protecting group present on the intermediate compound prior to reaction with amine and/or or removing at least one protecting group on the ring-opened reaction product following the reaction with amine.

In a further embodiment herein there is provided a process for making (2S,4S,5S, 7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate comprising reacting 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl]carbamate with 3-amino-2,2-dimethylpropanamide in the presence of 2-ethylhexanoic acid or cyclohexanecarboxylic acid, or a mixture thereof to provide (2S,4S,5S,7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate, or, converting the reaction product to provide (2S,4S,5S, 7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate.

In yet a further embodiment herein there is provided a process for making (2S,4S,5S,7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate comprising reacting 1,1-dimethylethyl [(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl]carbamate with 3-amino-2,2-dimethylpropanamide in the presence of a catalyst other than carboxylic acid catalyst; and, removing at least one protecting group on the 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl]carbamate and/or removing at least one protecting group on the reaction product with aqueous halogenic acid.

Similar to as stated above, it will be understood herein that the "removing at least one protecting group on the 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl]carbamate and/or removing at least one protecting group on the reaction product with aqueous halogenic acid" can comprise removing at least one protecting group present on the 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl]carbamate prior to reaction with 3-amino-2,2-dimethylpropanamide and/or or removing at least one protecting group on the reaction product following the reaction with 3-amino-2,2-dimethylpropanamide.

DETAILED DESCRIPTION OF THE INVENTION

Figure 1:
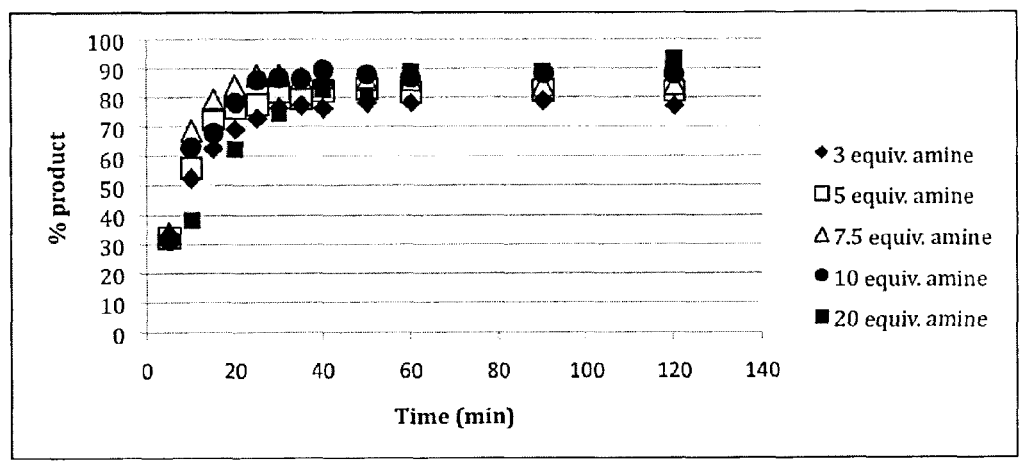
FIGS. 1-5 present experimental data in graphical form (Graphs 1-5) illustrating embodiments of the ring-opening process herein; and, FIGS. 6-9 present experimental data in bar graph form (Graph 6) and in bar graph form illustrating embodiments of the deprotecting step of the ring-opening process herein.

There is provided in a first embodiment herein a lactone and/or lactam ring-opening process in the presence of at least one carboxylic acid.

It will be understood herein that any lactone ring-containing and/or lactam ring-containing compound, ring-opened products thereof, renin-inhibitor compounds therefrom, or pharmaceutically acceptable or unacceptable salts of any of the aforesaid, described herein can be protected by one or more of any of the protecting groups described herein or any protecting group(s) that are known to those skilled in the art.

It will also be understood herein that any compound described herein may also describe any of its pharmaceutically acceptable salt(s) and/or any pharmaceutically unacceptable salt(s) thereof.

Lactone ring-containing compound and/or lactam ring-containing compound can comprise any compound containing at least one lactone and/or at least one lactam ring.

The expression "lactone ring-containing compound" as used herein is understood to be equivalent to "lactone-containing compound".

The expression "lactam ring-containing compound is understood to be equivalent to "lactam-containing compound".

It will be understood herein that the lactone ring-opening process described herein for the opening of a lactone ring with amine (as described herein) to produce δ-amino-γ-hydroxy-ω-aryl-alkanoic acid amide of the general formula (I), its salts, aliskiren and/or any intermediate thereto can be conducted in the manner described herein regardless of the synthesis route employed, and any known lactone opening step in the synthesis of aliskiren, its salts, or the δ-amino-γ-hydroxy-ω-aryl-alkanoic acid amide of the general formula (I) can be conducted in the manner described herein.

The term "removing" with regard to protecting group(s) is understood to be equivalent to the term "deprotecting" with regard to protecting group(s).

The term "intermediate" as used herein with regard to δ-amino-γ-hydroxy-ω-aryl-alkanoic acid amide can comprise an immediate precursor to δ-amino-γ-hydroxy-ω-aryl-alkanoic acid amide, or can comprise a compound which when reacted as described herein must still be converted to provide δ-amino-γ-hydroxy-ω-aryl-alkanoic acid amide.

U.S. Pat. No. 5,559,111, the contents of which are incorporated herein in their entirety, and the definitions of $R^1$-$R^8$ described herein are understood to be interchangeable in any manner with the definitions of $R_1$-$R_8$ as defined in U.S. Pat. No. 5,559,111 as are any of the corresponding definitions for moieties in U.S. Pat. No. 5,559,111.

It will be understood herein that any listing of members of a recited group can comprise, in one non-limiting embodiment, a combinations of any of the members of said recited group. Further, it will be understood herein that any separate listings of members of any of the same one component herein, e.g., separate listings of members of lactone ring containing and/or lactam ring-containing compound, amine, catalyst, solvent, and the like, can comprise combinations of any members from separate listings of the same one component.

It is understood herein that any recitation of ranges can comprise any combination of endpoints of said ranges and any sub ranges there between.

In one specific embodiment herein the δ-amino-γ-hydroxy-ω-aryl-alkanoic acid amide comprises the formula (II):

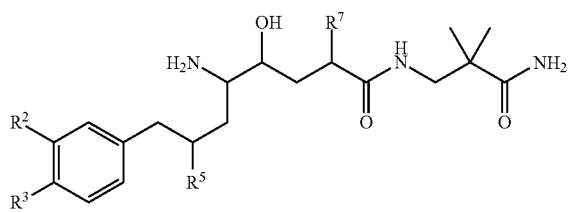

wherein $R^7$ is hydrogen, $C_{1-7}$ alkyl, $C_{3-8}$ cycloalkyl or benzyl, $R^2$ is halogen, hydroxyl, $C_{1-6}$ halogenalkyl, $C_{1-6}$ alkoxy-$C_{1-6}$ alkyloxy or $C_{1-6}$ alkoxy-$C_{1-6}$ alkyl; $R^3$ is halogen, hydroxyl, $C_{1-4}$ alkyl or $C_{1-4}$ alkoxy, or a salt thereof.

Preferably, the compound according to the formula (II) has the following stereochemistry:

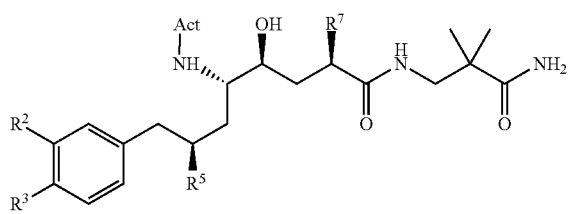

The reaction of any of the lactone ring-containing and/or lactam ring-containing compound, the intermediate compound, 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl] carbamate or any such compounds as described herein, with amine, as described herein, may in some non-limiting embodiments, take place under standard conditions for the formation of an amide from a lactone, e.g., in an appropriate solvent or solvent mixture, e.g., in an ether, such as tert-butyl methyl ether, preferably in the presence of a bifunctional catalyst with a weak acidic and a weak basic group, e.g. 2-hydroxypyridine or proline, in the presence of an appropriate base, e.g. a tertiary nitrogen base, such as triethylamine, at appropriate temperatures e.g. in the range from 0° C. to the reflux temperature of the reaction mixture, e.g. from 0 to 85° C.

In another specific embodiment herein the δ-amino-γ-hydroxy-ω-aryl-alkanoic acid amide is the formula (III):

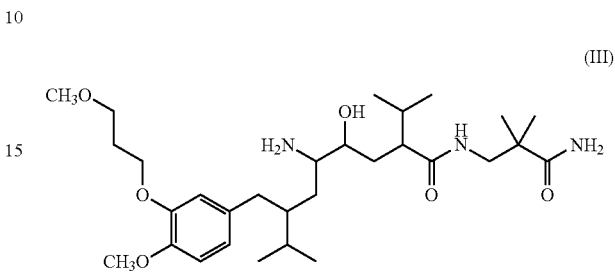

or salt thereof.

In a specific embodiment of the invention, amide (III) is aliskiren, i.e., amide (IIIa), having the stereochemical configuration:

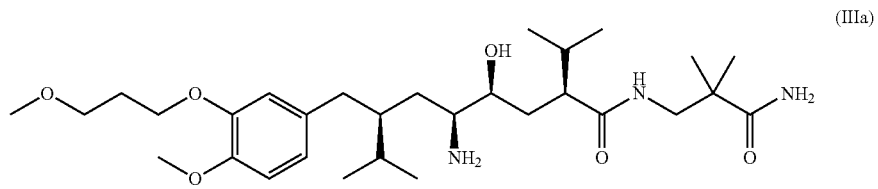 [SMILES: COCCCOc1cc(C[C@@H](C[C@H](N)[C@@H](O)C[C@H](C(=O)NCC(C)(C)C(N)=O)C(C)C)C(C)C)ccc1OC]

As used herein the following terms and expression are defined and exemplified below.

Aryl and aryl in aryl-lower alkoxy, aryl-lower alkyl and the like is, for example, phenyl or naphthyl that is unsubstituted or mono-, di- or tri-substituted by lower alkyl, lower alkoxy, hydroxy, lower alkylamino, di-lower alkylamino, halogen and/or by trifluoromethyl.

Cycloalkoxy and cycloalkoxy in cycloalkoxy-lower alkoxy and cycloalkoxy in cycloalkoxy-lower alkyl is, for example, 3- to 8-membered, preferably 3-, 5- or 6-membered, cycloalkoxy, such as cyclopropyloxy, cyclopentyloxy, cyclohexyloxy, also cyclobutyloxy, cycloheptyloxy or cyclooctyloxy.

Cycloalkoxy-lower alkyl is, for example, 3- to 8-membered, preferably 5- or 6-membered cycloalkoxy-$C_1$-$C_4$ lower alkyl, such as cyclopentyloxy- or cyclohexyloxy-methyl, 2-cyclopentyloxy- or 2-cyclohexyloxy-ethyl, 2- or 3-cyclopentyloxy- or 2- or 3-cyclohexyloxy-propyl, 2-cyclopentyloxy- or 2-cyclohexyloxy-2-methyl-propyl, 2-cyclopentyloxy- or 2-cyclohexyloxy-2-ethyl-butyl or 4-cyclopentyloxy- or 4-cyclohexyloxy-butyl.

Cycloalkyl is, for example, 3- to 8-membered, preferably 3-, 5- or 6-membered, cycloalkyl, such as cyclopropyl, cyclopentyl, cyclohexyl, also cyclobutyl, cycloheptyl or cyclooctyl.

Free or esterified or amidated carboxy-lower alkoxy is, for example, carboxy-lower alkoxy, lower alkoxycarbonyl-lower alkoxy, carbamoyl-lower alkoxy or N-mono- or N,N-di-lower alkylcarbamoyl-lower alkoxy.

Optionally lower alkanoylated, halogenated or sulfonylated hydroxy-lower alkoxy is, for example, lower alkanoyloxy-lower alkyl, hydroxy-lower alkoxy, halo-(hydroxy)-lower alkoxy or lower alkanesulfonyl-(hydroxy)-lower alkoxy.

Amino-lower alkyl that is unsubstituted or substituted by lower alkyl, lower alkanoyl and/or by lower alkoxycarbonyl is, for example, amino-lower alkyl, lower alkylamino-lower alkyl, di-lower alkylamino-lower alkyl, lower alkanoylamino-lower alkyl or lower alkoxycarbonylamino-lower alkyl.

Amino-lower alkoxy that is unsubstituted or substituted by lower alkyl, lower alkanoyl and/or by lower alkoxycarbonyl is, for example, amino-lower alkoxy, lower alkylamino-lower alkoxy, di-lower alkylamino-lower alkoxy, lower alkanoylamino-lower alkoxy or lower alkoxycarbonylamino-lower alkoxy.

Optionally S-oxidised lower alkylthio-lower alkoxy is, for example, lower alkylthio-lower alkoxy or lower alkanesulfonyl-lower alkoxy.

Optionally hydrogenated heteroaryl-lower alkoxy is, for example, optionally partially hydrogenated or N-oxidised pyridyl-lower alkoxy, thiazolyl-lower alkoxy or especially morpholino-lower alkoxy.

Optionally hydrogenated heteroarylthio-lower alkoxy is, for example, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy or pyrimidinylthio-lower alkoxy.

Free or esterified or amidated carboxy-lower alkyl is, for example, carboxy-lower alkyl, lower alkoxycarbonyl-lower alkyl, carbamoyl-lower alkyl or N-mono- or N,N-di-lower alkylcarbamoyl-lower alkyl.

Optionally halogenated lower alkyl is, for example, lower alkyl or polyhalo-lower alkyl.

Optionally halogenated lower alkoxy is, for example, lower alkoxy or polyhalo-lower alkoxy.

Optionally S-oxidised lower alkylthio-lower alkyl is, for example, lower alkylthio-lower alkyl or lower alkanesulfonyl-lower alkyl.

Optionally S-oxidised lower alkylthio-lower alkoxy is, for example, lower alkylthio-lower alkoxy or lower alkanesulfonyl-lower alkoxy.

Optionally hydrogenated heteroaryl-lower alkyl is, for example, optionally partially hydrogenated or N-oxidised pyridyl-lower alkyl.

Optionally hydrogenated heteroarylthio-lower alkyl is, for example, thiazolylthio-lower alkyl or thiazolinylthio-lower alkyl, imidazolylthio-lower alkyl, optionally N-oxidised pyridylthio-lower alkyl or pyrimidinylthio-lower alkyl.

Amino-lower alkyl that is unsubstituted or N-mono- or N,N-di-lower alkylated, -lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene is, for example, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl.

Optionally S-oxidised lower alkylthio-lower alkoxy is, for example, lower alkylthio-lower alkoxy or lower alkanesulfonyl-lower alkoxy.

Amino-lower alkoxy that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene is, for example, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothio-morpholino-lower alkoxy.

Unsubstituted or N-mono- or N,N-di-lower alkylated or N-lower alkanoylated amino is, for example, amino, lower alkylamino, di-lower alkylamino or lower alkanoylamino.

Free or aliphatically esterified or etherified hydroxy-lower alkyl is, for example, hydroxy-lower alkyl, lower alkanoyloxy-lower alkyl, lower alkoxy-lower alkyl or lower alkenyloxy-lower alkyl.

Amino-lower alkyl that is unsubstituted or N-lower alkanoylated, N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated aza-lower alkylene, by oxa-lower alkylene or by optionally S-oxidised thia-lower alkylene, is, for example, amino-lower alkyl, lower alkanoylamino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxy-piperidino-lower alkyl, piperazino-, N'-lower alkylpiperazino- or N'-lower alkanoylpiperazino-lower alkyl, unsubstituted or lower alkylated morpholino-lower alkyl, such as morpholino-lower alkyl or dimethylmorpholino-lower alkyl, or optionally S-oxidised thio-morpholino-lower alkyl, such as thiomorpholino-lower alkyl or S,S-dioxothiomorpholino-lower alkyl.

Free or esterified or amidated dicarboxy-lower alkyl is, for example, dicarboxy-lower alkyl, di-lower alkoxycarbonyl-lower alkyl, dicarbamoyl-lower alkyl or di-(N-mono- or N,N-di-lower alkylcarbamoyl)-lower alkyl.

Free or esterified or amidated carboxy-(hydroxy)-lower alkyl is, for example, carboxy-(hydroxy)-lower alkyl, lower alkoxycarbonyl-(hydroxy)-lower alkyl or carbamoyl-(hydroxy)-lower alkyl.

Free or esterified or amidated carboxycycloalkyl-lower alkyl is, for example, 5- or 6-membered carboxycycloalkyl-lower alkyl, lower alkoxycarbonylcycloalkyl-lower alkyl, carbamoylcycloalkyl-lower alkyl, or N-mono- or N,N-di-lower alkylcarbamoylcyclo-alkyl-lower alkyl.

Unsubstituted or N-mono- or N,N-di-lower alkylated sulfamoyl-lower alkyl is, for example, sulfamoyl-lower alkyl, lower alkylsulfamoyl-lower alkyl or di-lower alkyl-sulfamoyl-lower alkyl.

Unsubstituted or N-mono- or N,N-di-lower alkylated thiocarbamoyl-lower alkyl is, for example, thiocarbamoyl-lower alkyl, lower alkylthiocarbamoyl-lower alkyl or di-lower alkylthiocarbamoyl-lower alkyl, such as N,N-dimethylthiocarbamoylmethyl.

Heteroaryl that is optionally oxo-substituted, bonded via a carbon atom and optionally hydrogenated, and such a heteroaryl in a lower alkyl that is substituted by heteroaryl radicals that are optionally oxo-substituted, bonded via a carbon atom and optionally hydrogenated, contains as optionally hydrogenated heteroaryl radical, for example, an optionally partially hydrogenated and/or benzo-fused 5-membered aza-, diaza-, triaza-, oxadiaza- or tetraaza-aryl radical or a 6-membered aza- or diaza-aryl radical, and as lower alkyl radical, for example, $C_1$-$C_7$ alkyl, preferably $C_1$-$C_4$ alkyl, and is, for example, pyrrolidinyl-lower alkyl, e.g. oxopyrrolidinyl-$C_1$-$C_4$ alkyl, imidazolyl-lower alkyl, e.g. imidazol-4-yl-$C_1$-$C_4$ alkyl, benzimidazolyl-lower alkyl, e.g. benzimidazol-2-yl-$C_1$-$C_4$ alkyl, oxodiazolyl-lower alkyl, e.g. 1,2,4-oxadiazol-5-yl-$C_1$-$C_4$ alkyl, pyridyl-lower alkyl, e.g. pyridin-2-yl-$C_1$-$C_4$ alkyl, oxopiperidinyl-$C_1$-$C_4$ alkyl, dioxopiperidinyl-$C_1$-$C_4$ alkyl, oxothiazolyl-$C_1$-$C_4$ alkyl, oxo-oxazolinyl-$C_1$-$C_4$ alkyl or quinolinyl-lower alkyl, e.g. quinolin-2-yl-$C_1$-$C_4$ alkyl, also morpholinocarbonyl-lower alkyl or unsubstituted or N-lower alkanoylated piperidyl-lower alkyl.

Hereinbefore and hereinafter, lower radicals and compounds are to be understood as being, for example, those having up to and including 7, preferably up to and including 4, carbon atoms.

5- or 6-Membered carboxycycloalkyl-lower alkyl, lower alkoxycarbonylcycloalkyl-lower alkyl, carbamoylcycloalkyl-lower alkyl, N-mono- or N,N-di-lower alkylcarbamoylcyclo-alkyl-lower alkyl is, for example, ω-(1-carboxycycloalkyl)-$C_1$-$C_4$ alkyl, ω-(1-lower alkoxycarbonylcycloalkyl)-$C_1$-$C_4$ alkyl, ω-(1-carbamoylcycloalkyl)-$C_1$-$C_4$ alkyl, ω-(1-lower alkylcarbamoylcycloalkyl)-$C_1$-$C_4$ alkyl or ω-(1-di-lower alkylcarbamoylcycloalkyl)-$C_1$-$C_4$ alkyl, wherein cycloalkyl is, for example, cyclopentyl or cyclohexyl, lower alkoxycarbonyl is, for example, $C_1$-$C_4$ alkoxycarbonyl, such as methoxy- or ethoxycarbonyl, lower alkylcarbamoyl is, for example, $C_1$-$C_4$ alkylcarbamoyl, such as methylcarbamoyl, di-lower alkylcarbamoyl is, for example, di-$C_1$-$C_4$ alkylcarbamoyl, such as dimethylcarbamoyl, and lower alkyl is, for example, $C_1$-$C_4$ alkyl, such as methyl, ethyl, propyl or butyl, especially (1-carboxycyclopentyl)methyl.

5- or 6-Membered cycloalkoxy-lower alkoxy is, for example, cyclopentyloxy- or cyclohexyloxy-$C_1$-$C_4$ alkoxy, such as cyclopentyloxy- or cyclohexyloxy-methoxy, 2-cyclopentyloxy- or 2-cyclohexyloxy-ethoxy, 2- or 3-cyclopentyloxy- or 2- or 3-cyclohexyloxy-propyloxy or 4-cyclopentyloxy- or 4-cyclohexyloxy-butyloxy, especially cyclopentyloxy- or cyclohexyloxy-methoxy.

5- or 6-Membered cycloalkoxy-lower alkyl is, for example, cyclopentyloxy- or cyclohexyloxy-$C_1$-$C_4$ alkyl, such as cyclopentyloxy- or cyclohexyloxy-methyl, 2-cyclopentyloxy- or 2-cyclohexyloxy-ethyl, 2- or 3-cyclopentyloxy- or 2- or 3-cyclohexyloxy-propyl, 2-cyclopentyloxy- or 2-cyclohexyloxy-2-methyl-propyl, 2-cyclopentyloxy- or 2-cyclohexyloxy-2-ethyl-butyl or 4-cyclopentyloxy- or 4-cyclohexyloxy-butyl, especially cyclopentyloxy- or cyclohexyloxy-methyl.

Amino-lower alkoxy is, for example, amino-$C_1$-$C_4$ alkoxy, such as 2-aminoethoxy or 5-aminopentyloxy, also 3-aminopropyloxy or 4-aminobutyloxy.

Amino-lower alkyl is, for example, amino-$C_1$-$C_4$ alkyl, such as 2-aminoethyl, 3-aminopropyl or 4-aminobutyl.

Carbamoyl-(hydroxy)-lower alkyl is, for example, carbamoyl-$C_1$-$C_7$ (hydroxy)alkyl, such as 1-carbamoyl-2-hydroxyethyl.

Carbamoyl-lower alkoxy is, for example, carbamoyl-$C_1$-$C_4$ alkoxy, such as carbamoylmethoxy, 2-carbamoylethoxy, 3-carbamoylpropyloxy or 4-carbamoylbutyloxy, especially carbamoylmethoxy.

Carbamoyl-lower alkyl is, for example, carbamoyl-$C_1$-$C_7$ alkyl, such as carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoylbutyl, 1-carbamoylbutyl, 1-(1-carbamoyl-2-methyl)butyl or 3-(4-carbamoyl-2-methyl)butyl.

Carboxy-(hydroxy)-lower alkyl is, for example, carboxy-$C_1$-$C_7$ (hydroxy)alkyl, such as 1-carboxy-2-hydroxy-ethyl.

Carboxy-lower alkoxy is, for example, carboxy-$C_1$-$C_4$ alkoxy, such as carboxymethoxy, 2-carboxyethoxy, 2- or 3-carboxypropyloxy or 4-carboxybutyloxy, especially carboxy-methoxy.

Carboxy-lower alkyl is, for example, carboxy-$C_1$-$C_4$ alkyl, such as carboxymethyl, 2-carboxyethyl, 2- or 3-carboxypropyl, 2-carboxy-2-methyl-propyl, 2-carboxy-2-ethyl-butyl or 4-carboxybutyl, especially carboxymethyl.

Cyano-lower alkoxy is, for example, cyano-$C_1$-$C_4$ alkoxy, such as cyanomethoxy, 2-cyano-ethoxy, 2- or 3-cyanopropyloxy or 4-cyanobutyloxy, especially cyanomethoxy.

Cyano-lower alkyl is, for example, cyano-$C_1$-$C_4$ alkyl, such as cyanomethyl, 2-cyanoethyl, 2- or 3-cyanopropyl, 2-cyano-2-methyl-propyl, 2-cyano-2-ethyl-butyl or 4-cyanobutyl, especially cyanomethyl.

Di-(N-mono- or N,N-di-lower alkylcarbamoyl)-lower alkyl is, for example, di-(N-mono- or N,N-di-$C_1$-$C_4$ alkylcarbamoyl)-$C_1$-$C_4$ alkyl, such as 1,2-di-(N-mono- or N,N-di-$C_1$-$C_4$ alkylcarbamoyl)ethyl or 1,3-di-(N-mono- or N,N-di-$C_1$-$C_4$ alkylcarbamoyl)propyl.

Dicarbamoyl-lower alkyl is, for example, dicarbamoyl-$C_1$-$C_4$ alkyl, such as 1,2-dicarbamoylethyl or 1,3-dicarbamoylpropyl.

Dicarboxy-lower alkyl is, for example, dicarboxy-$C_1$-$C_4$ alkyl, such as 1,2-dicarboxyethyl or 1,3-dicarboxypropyl.

Dimethylmorpholino-lower alkoxy can be N-oxidised and is, for example, 2,6-dimethylmorpholino- or 3,5-dimethylmorpholino-$C_1$-$C_4$ alkoxy, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyloxy, 2-(2,6-dimethylmorpholino- or 3,5-dimethylmorpholino-3-methyl)propyloxy, or 1- or 2-[4-(2,6-dimethylmorpholino- or 3,5-dimethylmorpholino)]-butyloxy.

Dimethylmorpholino-lower alkyl can be N-oxidised and is, for example, 2,6-dimethylmorpholino- or 3,5-dimethylmorpholino-$C_1$-$C_4$ alkyl, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyl, 2-(2,6-dimethylmorpholino- or 3,5-dimethylmorpholino-3-methyl)-propyl, or 1- or 2-[4-(2,6-dimethylmorpholino- or 3,5-dimethylmorpholino)]-butyl.

Di-lower alkoxycarbonyl-lower alkyl is, for example, di-lower alkoxycarbonyl-$C_1$-$C_4$ alkyl, such as 1,2-dimethoxycarbonylethyl, 1,3-dimethoxycarbonylpropyl, 1,2-dimethoxycarbonylethyl or 1,3-diethoxycarbonylpropyl.

Di-lower alkylamino is, for example, di-$C_1$-$C_4$ alkylamino, such as dimethylamino, N-methyl-N-ethylamino, diethylamino, N-methyl-N-propylamino or N-butyl-N-methylamino.

Di-lower alkylamino-lower alkoxy is, for example, N,N-di-$C_1$-$C_4$ alkylamino-$C_1$-$C_4$ alkoxy, such as 2-dimethylaminoethoxy, 3-dimethylaminopropyloxy, 4-dimethylaminobutyloxy, 2-diethylaminoethoxy, 2-(N-methyl-N-ethyl-amino) ethoxy or 2-(N-butyl-N-methyl-amino)ethoxy.

Di-lower alkylamino-lower alkyl is, for example, N,N-di-$C_1$-$C_4$ alkylamino-$C_1$-$C_4$ alkyl, such as 2-dimethylaminoethyl, 3-dimethylaminopropyl, 4-dimethylaminobutyl, 2-diethylaminoethyl, 2-(N-methyl-N-ethyl-amino)ethyl or 2-(N-butyl-N-methyl-amino)ethyl.

Di-lower alkylcarbamoyl-lower alkoxy is, for example, N,N-di-$C_1$-$C_4$alkylcarbamoyl-$C_1$-$C_4$ alkoxy, such as methyl- or dimethyl-carbamoyl-$C_1$-$C_4$ alkoxy, such as N-methyl-, N-butyl- or N,N-dimethyl-carbamoylmethoxy, 2-(N-methylcarbamoyl)ethoxy, 2-(N-butylcarbamoyl)ethoxy, 2-(N,N-dimethylcarbamoyl)ethoxy, 3-(N-methylcarbamoyl)propyloxy, 3-(N-butylcarbamoyl)propyloxy, 3-(N,N-dimethylcarbamoyl)propyloxy or 4-(N-methylcarbamoyl)butyloxy, 4-(N-butylcarbamoyl)butyloxy or 4-(N,N-dimethylcarbamoyl)butyloxy, especially N-methyl-, N-butyl- or N,N-dimethyl-carbamoylmethoxy.

Di-lower alkylcarbamoyl-lower alkyl is, for example, N,N-di-$C_1$-$C_4$ alkylcarbamoyl-$C_1$-$C_4$ alkyl, such as 2-dimethylcarbamoylethyl, 3-dimethylcarbamoylpropyl, 2-dimethylcarbamoylpropyl, 2-(dimethylcarbamoyl-2-methyl)propyl or 2-(1-dimethylcarbamoyl-3-methyl)butyl.

Di-lower alkylsulfamoyl-lower alkyl is, for example, N,N-di-$C_1$-$C_4$ alkylsulfamoyl-$C_1$-$C_4$ alkyl, N,N-dimethylsulfamoyl-$C_1$-$C_4$ alkyl, such as N,N-dimethylsulfamoylmethyl, 2-(N,N-dimethylcarbamoyl)ethyl, 3-(N,N-dimethylcarbamoyl)propyl or 4-(N,N-dimethylcarbamoyl)butyl, especially N,N-dimethylcarbamoylmethyl.

Unsubstituted or N-lower alkanoylated piperidyl-lower alkyl is, for example, 1-$C_1$-$C_7$ lower alkanoylpiperidin-4-yl-$C_1$-$C_4$ alkyl, such as 1-acetylpiperidinylmethyl or 2-(1-acetylpiperidinyl)ethyl.

Optionally partially hydrogenated or N-oxidised pyridyl-lower alkoxy is, for example, optionally partially hydrogenated pyridyl- or N-oxidopyridyl-$C_1$-$C_4$ alkoxy, such as pyridyl- or N-oxidopyridyl-methoxy, 2-pyridylethoxy, 2- or 3-pyridylpropyloxy or 4-pyridylbutyloxy, especially 3- or 4-pyridylmethoxy.

Optionally partially hydrogenated or N-oxidised pyridyl-lower alkyl is, for example, optionally partially hydrogenated pyridyl- or N-oxidopyridyl-$C_1$-$C_4$ alkyl, such as pyridyl- or N-oxidopyridyl-methyl, 2-pyridylethyl, 2- or 3-pyridylpropyl or 4-pyridylbutyl, especially 3- or 4-pyridylmethyl.

Halo-(hydroxy)-lower alkoxy is, for example, halo-$C_2$-$C_7$ (hydroxy)alkoxy, especially halo-$C_2$-$C_4$ (hydroxy)alkoxy, such as 3-halo-, such as 3-chloro-2-hydroxy-propyloxy.

Hydroxy-lower alkoxy is, for example, hydroxy-$C_2$-$C_7$ alkoxy, especially hydroxy-$C_2$-$C_4$ alkoxy, such as 2-hydroxybutyloxy, 3-hydroxypropyloxy or 4-hydroxybutyloxy.

Hydroxy-lower alkyl is, for example, hydroxy-$C_2$-$C_7$ alkyl, especially hydroxy-$C_2$-$C_4$ alkyl, such as 2-hydroxyethyl, 3-hydroxypropyl or 4-hydroxybutyl.

Hydroxypiperidino-lower alkyl is, for example, 3- or 4-hydroxypiperidino-$C_1$-$C_4$ alkoxy, such as 3- or 4-hydroxypiperidinomethoxy, 2-(3- or 4-hydroxypiperidino)ethoxy, 3-(3- or 4-hydroxypiperidino)propyloxy or 4-(3- or 4-hydroxypiperidino)butyloxy.

Imidazolyl-lower alkyl is, for example, imidazolyl-$C_1$-$C_4$ alkyl, such as imidazol-4-yl-methyl, 2-(imidazol-4-yl)ethyl, 3-(imidazol-4-yl)propyl or 4-(imidazol-4-yl)butyl.

Imidazolyl-lower alkoxy is, for example, imidazolyl-$C_1$-$C_4$ alkoxy, such as imidazol-4-yl-methoxy, 2-(imidazol-4-yl)ethoxy, 3-(imidazol-4-yl)propyloxy or 4-(imidazol-4-yl)butyloxy.

Imidazolyl-lower alkyl is, for example, imidazolyl-$C_1$-$C_4$ alkyl, such as imidazol-4-yl-methyl, 2-(imidazol-4-yl)ethyl, 3-(imidazol-4-yl)propyl or 4-(imidazol-4-yl)butyl.

Morpholinocarbonyl-lower alkyl is, for example, morpholinocarbonyl-$C_1$-$C_4$ alkyl, such as 1-morpholinocarbonylethyl, 3-morpholinocarbonylpropyl, or 1-(morpholinocarbonyl-2-methyl)propyl.

Morpholino-lower alkoxy can be N-oxidised and is, for example, morpholino-$C_1$-$C_4$ alkoxy, such as 1-morpholinoethoxy, 3-morpholinopropyloxy, or 1-(morpholino-2-methyl)propyloxy.

Morpholino-lower alkyl can be N-oxidised and is, for example, morpholino-$C_1$-$C_4$ alkyl, such as morpholinomethyl, 2-morpholinoethyl, 3-morpholinopropyl or 1- or 2-(4-morpholino)butyl.

Lower alkanoyl is, for example, $C_1$-$C_7$ alkanoyl, especially $C_2$-$C_6$ alkanoyl, such as acetyl, propionyl, butyryl, isobutyryl or pivaloyl.

Lower alkanoylamino is, for example, N—$C_1$-$C_7$ alkanoylamino, such as acetylamino or pivaloylamino.

Lower alkanoylamino is, for example, N—$C_1$-$C_7$ alkanoylamino, such as acetylamino or pivaloylamino.

Lower alkanoylamino-lower alkyl is, for example, N—$C_1$-$C_4$ alkanoylamino-$C_1$-$C_4$ alkyl, such as 2-acetoxyaminoethyl.

Lower alkanoylamino-lower alkyl is, for example, N—$C_1$-$C_4$ alkanoylamino-$C_1$-$C_4$ alkyl, such as 2-acetoxyaminoethyl.

Lower alkanoyl-lower alkoxy (oxo-lower alkoxy) carries the lower alkanoyl group in a position higher than the α-position and is, for example, $C_1$-$C_7$ alkanoyl-$C_1$-$C_4$ alkoxy, such as 4-acetylbutoxy.

Lower alkanoyloxy-lower alkyl carries the lower alkanoyloxy group in a position higher than the α-position and is, for example, $C_1$-$C_7$ alkanoyloxy-$C_1$-$C_4$ alkyl, such as 4-acetoxybutyl.

Lower alkanesulfonyl-(hydroxy)-lower alkoxy is, for example, $C_1$-$C_7$ alkanesulfonyl-$C_1$-$C_4$(hydroxy)alkoxy, such as 3-methanesulfonyl-2-hydroxy-propyloxy.

Lower alkanesulfonyl-lower alkoxy is, for example, $C_1$-$C_7$ alkanesulfonyl-$C_1$-$C_4$ alkoxy, such as methanesulfonylmethoxy or 3-methanesulfonyl-2-hydroxy-propyloxy.

Lower alkanesulfonylamino-lower alkoxy is, for example, $C_1$-$C_7$ alkanesulfonylamino-$C_1$-$C_4$ alkoxy, such as ethanesulfonylaminomethoxy, 2-ethanesulfonylaminoethoxy, 3-ethanesulfonylaminopropyloxy or 3-(1,1-dimethylethanesulfonylamino)propyloxy.

Lower alkanesulfonylamino-lower alkyl is, for example, $C_1$-$C_7$ alkanesulfonylamino-$C_1$-$C_4$ alkyl, such as ethanesulfonylaminomethyl, 2-ethanesulfonylaminoethyl, 3-ethanesulfonylaminopropyl or 3-(1,1-dimethylethanesulfonylamino)propyl.

Lower alkanesulfonyl-lower alkyl is, for example, $C_1$-$C_7$ alkanesulfonyl-$C_1$-$C_4$ alkyl, such as ethanesulfonylmethyl, 2-ethanesulfonylethyl, 3-ethanesulfonylpropyl or 3-(1,1-dimethylethanesulfonyl)propyl.

Lower alkenyl is, for example, $C_2$-$C_7$ alkenyl, such as vinyl or allyl.

Lower alkenyloxy is, for example, $C_2$-$C_7$ alkenyloxy, such as allyloxy.

Lower alkenyloxy-lower alkoxy is, for example, $C_2$-$C_7$ alkenyloxy-$C_1$-$C_4$ alkoxy, such as allyloxymethoxy.

Lower alkenyloxy-lower alkyl is, for example, $C_2$-$C_7$ alkenyloxy-$C_1$-$C_4$ alkyl, such as allyloxymethyl.

Lower alkoxy is, for example, $C_1$-$C_7$ alkoxy, preferably $C_1$-$C_5$ alkoxy, such as methoxy, ethoxy, propyloxy, isopropyloxy, butyloxy, isobutyloxy, secondary butyloxy, tertiary butyloxy, pentyloxy or a hexyloxy or heptyloxy group.

Lower alkoxycarbonyl is, for example, $C_1$-$C_7$ alkoxycarbonyl, preferably $C_1$-$C_5$ alkoxycarbonyl, such as methoxycarbonyl, ethoxycarbonyl, propyloxycarbonyl, isopropyloxycarbonyl, butyloxycarbonyl, isobutyloxycarbonyl, secondary butyloxycarbonyl, tertiary butyloxy, pentyloxycarbonyl or a hexyloxycarbonyl or heptyloxycarbonyl group.

Lower alkoxycarbonyl-(hydroxy)-lower alkyl is, for example, $C_1$-$C_4$ alkoxycarbonyl-$C_1$-$C_7$ (hydroxy)alkyl, such as 1-methoxycarbonyl- or 1-ethoxycarbonyl-2-hydroxyethyl.

Lower alkoxycarbonylamino-lower alkoxy is, for example, $C_1$-$C_7$ alkoxycarbonylamino-$C_2$-$C_7$ alkoxy, preferably $C_2$-$C_5$ alkoxycarbonylamino-$C_2$-$C_7$ alkoxy, such as methoxycarbonylamino-$C_2$-$C_7$ alkoxy, ethoxycarbonylamino-$C_2$-$C_7$ alkoxy, propyloxycarbonylamino-$C_2$-$C_7$ alkoxy, isobutyloxycarbonylamino-$C_2$-$C_7$ alkoxy, butyloxycarbonylamino-$C_2$-$C_7$ alkoxy, isobutyloxycarbonylamino-$C_2$-$C_7$ alkoxy, secondary butyloxycarbonylamino-$C_2$-$C_7$ alkoxy or tertiary butyloxyamino-$C_2$-$C_7$ alkoxy, wherein $C_2$-$C_7$ alkoxy is, for example, methoxy, ethoxy, propyloxy, butyloxy, pentyloxy or hexyloxy.

Lower alkoxycarbonylamino-lower alkyl is, for example, $C_1$-$C_7$ alkoxycarbonylamino-$C_2$-$C_7$ alkyl, preferably $C_2$-$C_5$ alkoxycarbonylamino-$C_2$-$C_7$ alkyl, such as methoxycarbonyl-$C_2$-$C_7$ alkyl, ethoxycarbonylamino-$C_2$-$C_7$-alkyl, propyloxycarbonylamino-$C_2$-$C_7$-alkyl isopropyloxycarbonylamino-$C_2$-$C_7$ alkyl, butyloxycarbonylamino-$C_2$-$C_7$ alkyl, isobutyloxycarbonylamino-$C_2$-$C_7$ alkyl, secondary butyloxycarbonylamino-$C_2$-$C_7$ alkyl or tertiary butyloxyamino-$C_2$-$C_7$ alkyl, wherein $C_2$-$C_7$ alkyl is, for example, methyl, ethyl, propyl, butyl, pentyl or hexyl.

Lower alkoxycarbonyl-lower alkoxy is, for example, $C_1$-$C_4$ alkoxycarbonyl-$C_1$-$C_4$ alkoxy, such as methoxycarbonyl- or ethoxycarbonyl-methoxy, 2-methoxycarbonyl- or 2-ethoxycarbonyl-ethoxy, 2- or 3-methoxycarbonyl- or 2- or 3-ethoxycarbonyl-propyloxy or 4-methoxycarbonyl- or 4-ethoxycarbonyl-butyloxy, especially methoxycarbonyl- or ethoxycarbonyl-methoxy or 3-methoxycarbonyl- or 3-ethoxycarbonyl-propyloxy.

Lower alkoxycarbonyl-lower alkyl is, for example, $C_1$-$C_4$ alkoxycarbonyl-$C_1$-$C_4$ alkyl, such as methoxycarbonyl- or ethoxycarbonyl-methoxy, 2-methoxycarbonyl- or 2-ethoxycarbonyl-ethoxy, 3-methoxycarbonyl- or 3-ethoxycarbonyl-propyloxy or 4-ethoxycarbonylbutyloxy.

Lower alkoxy-lower alkenyl is, for example, $C_1$-$C_4$ alkoxy-$C_2$-$C_4$ alkenyl, such as 4-methoxybut-2-enyl.

Lower alkoxy-lower alkenyloxy is, for example, $C_1$-$C_4$ alkoxy-$C_2$-$C_4$ alkenyloxy, such as 4-methoxybut-2-enyloxy.

Lower alkoxy-lower alkoxy is, for example, $C_1$-$C_4$ alkoxy-$C_2$-$C_4$ alkoxy, such as 2-methoxy-, 2-ethoxy- or 2-propyloxy-ethoxy, 3-methoxy- or 3-ethoxy-propyloxy or 4-methoxybutyloxy, especially 3-methoxypropyloxy or 4-methoxybutyloxy.

Lower alkoxy-lower alkoxy-lower alkyl is, for example, $C_1$-$C_4$ alkoxy-$C_1$-$C_4$ alkoxy-$C_1$-$C_4$ alkyl, such as 2-methoxy-, 2-ethoxy- or 2-propyloxy-ethoxymethyl, 2-(2-methoxy-, 2-ethoxy- or 2-propyloxy-ethoxy)ethyl, 3-(3-methoxy- or 3-ethoxy-propyloxy)propyl or 4-(2-methoxybutyloxy)butyl, especially 2-(3-methoxypropyloxy)ethyl or 2-(4-methoxybutyloxy)ethyl.

Lower alkoxy-lower alkyl is, for example, $C_1$-$C_4$ alkoxy-$C_1$-$C_4$ alkyl, such as ethoxymethyl, propyloxymethyl, butyloxymethyl, 2-methoxy-, 2-ethoxy- or 2-propyloxy-ethyl, 3-methoxy- or 3-ethoxy-propyl or 4-methoxybutyl, especially 3-methoxypropyl or 4-methoxybutyl.

Lower alkoxypiperidino-lower alkyl is, for example, piperidino-, hydroxypiperidino- or lower alkoxypiperidino-$C_1$-$C_4$ alkyl, such as piperidinomethyl, 4-hydroxypiperidinomethyl or 4-$C_1$-$C_4$ alkoxy-, such as 4-methoxypiperidinomethyl.

Lower alkoxypiperidino-lower alkyl is, for example, $C_1$-$C_4$ alkoxypiperidino-$C_1$-$C_4$ alkyl, such as 4-$C_1$-$C_4$ alkoxy-piperidinomethyl, especially 4-methoxypiperidinomethyl.

Lower alkyl may be straight-chained or branched and/or bridged and is, for example, corresponding $C_1$-$C_7$ alkyl, such as methyl, ethyl, propyl, isopropyl, butyl, isobutyl, secondary butyl or tertiary butyl, or a pentyl, hexyl or heptyl group. Lower alkyl $R^2$ or $R^3$ is especially $C_2$-$C_7$ alkyl, lower alkyl $R^5$ or $R^7$ is especially branched $C_3$-$C_7$ alkyl and lower alkyl $R^8$ or $R^3$ is, for example, straight-chained, branched or bridged $C_3$-$C_7$ alkyl.

Lower alkylamino is, for example, $C_1$-$C_4$ alkylamino, such as methylamino, ethylamino, propylamino, butylamino, isobutylamino, secondary butylamino or tertiary butylamino.

Lower alkylamino-lower alkoxy is, for example, $C_1$-$C_4$ alkylamino-$C_1$-$C_4$ alkoxy, such as propylaminomethoxy, 2-methylamino-, 2-ethylamino-, 2-propylamino- or 2-butylamino-ethoxy, 3-ethylamino- or 3-propylamino-propyloxy or 4-methylaminobutoxy.

Lower alkylamino-lower alkyl is, for example, $C_1$-$C_4$ alkylamino-$C_1$-$C_4$ alkyl, such as propylaminomethyl, 2-methylamino-, 2-ethylamino-, 2-propylamino- or 2-butylaminoethyl, 3-ethylamino- or 3-propylamino-propyl or 4-methylaminobutyl.

Lower alkylcarbamoyl-lower alkoxy is, for example, N—$C_1$-$C_7$ alkylcarbamoyl-$C_1$-$C_4$ alkoxy, such as methyl- or dimethyl-carbamoyl-$C_1$-$C_4$ alkoxy, e.g. methylcarbamoylmethoxy, 2-methylcarbamoylethoxy or 3-methylcarbamoylpropyloxy.

Lower alkylenedioxy is, for example, methylenedioxy or ethylenedioxy, but can also be 1,3- or 1,2-propylenedioxy.

Lower alkylsulfamoyl-lower alkyl is, for example, N—$C_1$-$C_7$ alkylsulfamoyl-$C_1$-$C_4$ alkyl, such as N-methyl-, N-ethyl-, N-propyl- or N-butyl-sulfamoyl-$C_1$-$C_4$ alkyl, such as N-methyl-, N-ethyl-, N-propyl- or N-butyl-sulfamoylmethyl, 2-(N-methylsulfamoyl)ethyl, 2-(N-butylsulfamoyl)ethyl, 3-(N-methylsulfamoyl)propyl, 3-(N-butylsulfamoyl)propyl, or 4-(N-methylsulfamoyl)butyl, 4-(N-butylsulfamoyl)butyl or 4-(N,N-dimethylsulfamoyl)butyl, especially N-methyl-, N-butyl- or N,N-dimethyl-sulfamoylmethyl.

Lower alkylthio-(hydroxy)-lower alkoxy is, for example, N—$C_1$-$C_4$ alkylthio-$C_1$-$C_4$ (hydroxy)alkoxy, such as 2-hydroxy-3-methylthiopropyloxy.

Oxazolyl-lower alkyl is, for example, oxazolyl-$C_1$-$C_4$ alkyl, such as 2-(1,2,4-oxadiazol-5-yl)ethyl, 3-(1,2,4-oxadiazol-5-yl)propyl or 4-(1,2,4-oxadiazol-5-yl)butyl.

Lower alkylthio-lower alkoxy is, for example, N—$C_1$-$C_4$ alkylthio-$C_1$-$C_4$ alkoxy, such as methylthio-$C_1$-$C_4$ alkoxy, e.g. methylthiomethoxy, 2-methylthioethoxy or 3-methylthiopropyloxy.

Lower alkylthio-lower alkyl is, for example, N—$C_1$-$C_4$ alkylthio-$C_1$-$C_4$ alkyl, such as methylthio-$C_1$-$C_4$ alkyl, e.g. methylthiomethyl, 2-methylthioethyl or 3-methylthiopropyl.

N'-Lower alkanoylpiperazino-lower alkoxy is, for example, N'-lower alkanoylpiperazino-$C_1$-$C_4$alkoxy, such as 4-acetylpiperazinomethoxy.

N'-Lower alkanoylpiperazino-lower alkyl is, for example, N'—$C_2$-$C_7$ lower alkanoylpiperazino-$C_1$-$C_4$ alkyl, such as 4-acetylpiperazinomethyl.

N'-Lower alkylpiperazino-lower alkyl is, for example, N'—$C_1$-$C_4$ alkylpiperazino-$C_1$-$C_4$ alkyl, such as 4-methylpiperazinomethyl.

Oxo-lower alkoxy is, for example, oxo-$C_1$-$C_4$ alkoxy, such as 3,3-dimethyl-2-oxo-butyloxy.

piperazino-lower alkyl is, for example, piperazino-$C_1$-$C_4$ alkyl, such as piperazinomethyl, 2-piperazinoethyl or 3-piperazinopropyl.

Piperidino-lower alkoxy is, for example, piperidino-$C_1$-$C_4$ alkoxy, such as piperidinomethoxy, 2-piperidinoethoxy or 3-piperidinopropyloxy.

Piperidino-lower alkyl is, for example, piperidino-$C_1$-$C_4$ alkyl, such as piperidinomethyl, 2-piperidinoethyl or 3-piperidinopropyl.

Polyhalo-lower alkanesulfonylamino-lower alkoxy is, for example, trifluoro-$C_1$-$C_7$ alkanesulfonyl-$C_1$-$C_4$ alkoxy, such as trifluoromethanesulfonylaminobutyloxy.

Polyhalo-lower alkanesulfonylamino-lower alkyl is, for example, trifluoro-$C_1$-$C_7$ alkanesulfonyl-$C_1$-$C_4$ alkyl, such as trifluoromethanesulfonylaminobutyl.

Pyrimidinyl-lower alkoxy is, for example, pyrimidinyl-$C_1$-$C_4$ alkoxy, such as pyrimidinylmethoxy, 2-pyrimidinylethoxy or 3-pyrimidinylpropyloxy.

Pyrimidinyl-lower alkyl is, for example, pyrimidinyl-$C_1$-$C_4$ alkyl, such as pyrimidinylmethyl, 2-pyrimidinylethyl or 3-pyrimidinylpropyl.

Pyrrolidino-lower alkoxy is, for example, pyrrolidino-$C_2$-$C_4$ alkoxy, such as 2-pyrrolidinoethoxy or 3-pyrrolidinopropyloxy.

Pyrrolidino-lower alkyl is, for example, pyrrolidino-$C_1$-$C_4$ alkyl, such as pyrrolidinomethyl, 2-pyrrolidinoethyl or 3-pyrrolidinopropyl.

S,S-Dioxothiomorpholino-lower alkyl is, for example, S,S-dioxothiomorpholino-$C_1$-$C_4$ alkyl, such as S,S-dioxothiomorpholinomethyl or 2-(S,S-dioxo)thiomorpholinoethyl.

S-Oxothiomorpholino-lower alkyl is, for example, S-oxothiomorpholino-$C_1$-$C_4$ alkyl, such as S-oxothiomorpholinomethyl or 2-(S-oxo)thiomorpholinoethyl.

Sulfamoyl-lower alkyl is, for example, sulfamoyl-$C_1$-$C_4$ alkyl, such as sulfamoyl-$C_1$-$C_4$alkyl, such as sulfamoylmethyl, 2-sulfamoylethyl, 3-sulfamoylpropyl or 4-sulfamoylbutyl.

Tetrazolyl-lower alkyl is, for example, tetrazolyl-$C_1$-$C_4$ alkyl, such as tetrazol-5-ylmethyl, 2-(tetrazol-5-yl)ethyl, 3-(tetrazol-5-yl)propyl or 4-(tetrazol-4-yl)butyl.

Thiazolinyl-lower alkoxy is, for example, thiazolinyl-$C_1$-$C_4$ alkoxy, such as thiazolinylmethoxy, 2-thiazolinylmethoxy or 3-thiazolinylpropyloxy.

Thiazolinyl-lower alkyl is, for example, thiazolinyl-$C_1$-$C_4$ alkyl, such as thiazolinylmethyl, 2-thiazolinylethyl or 3-thiazolinylpropyl.

Thiazolyl-lower alkoxy is, for example, thiazolyl-$C_1$-$C_4$ alkoxy, such as thiazolylmethoxy, 2-thiazolylethoxy or 3-thiazolylpropyloxy.

Thiazolyl-lower alkyl is, for example, thiazolyl-$C_1$-$C_4$ alkyl, such as thiazolylmethyl, 2-thiazolylethyl or 3-thiazolylpropyl.

Thiomorpholino-lower alkyl or S,S-dioxothiomorpholino-lower alkyl is, for example, thiomorpholino-$C_1$-$C_4$ alkyl, such as -methyl or -ethyl, or S,S-dioxothiomorpholino-$C_1$-$C_4$ alkyl, such as -methyl or -ethyl.

Depending on whether asymmetric carbon atoms are present, the compounds described herein can be present as mixtures of isomers, especially as racemates, or in the form of pure isomers, especially optical antipodes.

Salts of compounds having salt-forming groups are especially acid addition salts, salts with bases or, where several salt-forming groups are present, can also be mixed salts or internal salts.

Salts are especially the pharmaceutically acceptable or non-toxic salts of compounds of formula I.

Such salts are formed, for example, by compounds of formula (I) having an acid group, for example a carboxy group or a sulfo group, and are, for example, salts thereof with suitable bases, such as non-toxic metal salts derived from metals of groups Ia, Ib, IIa and IIb of the Periodic Table of the Elements, for example alkali metal salts, especially lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium bases, for example with methyl-, ethyl-, diethyl- or triethyl-amine, mono-, his- or tris-(2-hydroxy-lower alkyl)-amines, such as ethanol-, diethanol- or triethanol-amine, tris-(hydroxymethyl)-methylamine or 2-hydroxy-tert-butylamines, N,N-di-lower alkyl-N-(hydroxy-lower alkyl)-amines, such as N,N-dimethyl-N-(2-hydroxyethyl)-amine, or N-methyl-D-glucamine, or quaternary ammonium hydroxides, such as tetrabutylammonium hydroxide. The compounds of formula (I) having a basic group, for example an amino group, can form acid addition salts, for example with suitable inorganic acids, for example hydrohalic acids, such as hydrochloric acid or hydrobromic acid, or sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic (=pamoic) acid, nicotinic acid or isonicotinic acid, as well as with amino acids, such as the .alpha.-amino acids mentioned hereinbefore, and with methanesulfonic acid, ethanesulfonic acid, 2-hydroxyethanesulfonic acid, ethane-1,2-disulfonic acid, benzenesulfonic acid, 4-toluenesulfonic acid, naphthalene-2-sulfonic acid, 2- or 3-phosphoglycerate, glucose-6-phosphate, or N-cyclohexylsulfamic acid (forming cyclamates) or with other acidic organic compounds, such as ascorbic acid. Compounds of formula I having acid and basic groups can also form internal salts.

In one embodiment herein for isolation and purification purposes it is also possible to use pharmaceutically unacceptable salts.

The groups of compounds mentioned below are not to be regarded as exclusive; rather, for example in order to replace general definitions with more specific definitions, parts of those groups of compounds can be interchanged or exchanged for the definitions given above, or omitted, as appropriate.

The invention relates especially to making compounds of formula (I) wherein $R^1$ is hydrogen, hydroxy, lower alkoxy, cycloalkoxy, lower alkoxy-lower alkoxy, carboxy-lower alkoxy, lower alkoxy-carbonyl-lower alkoxy, carbamoyl-lower alkoxy or N-mono- or N,N-di-lower alkylcarbamoyl-lower alkoxy, $R^2$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoylamino-lower alkyl, lower alkoxycarbonyl-amino-lower alkyl, amino-lower alkoxy, lower alkylamino-lower alkoxy, di-lower alkylamino-lower alkoxy, lower alkanoylamino-lower alkoxy, lower alkoxycarbonyl-amino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, carbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R^3$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolyl-thio-lower alkyl or thiazolinylthio-lower alkyl, imidazolylthio-lower alkyl, optionally N-oxidised pyridylthio-lower alkyl, pyrimidinylthio-lower alkyl, amino-lower alkyl, lower alkylamino-lower alkyl, di-lower alkylamino-lower alkyl, lower alkanoyl-amino-lower alkyl, lower alkanesulfonylamino-lower alkyl, polyhalo-lower alkane-sulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothio-morpholino-lower alkyl, cyano-lower alkyl, carboxy-lower alkyl, lower alkoxy-carbonyl-lower alkyl, carbamoyl-lower alkyl, N-mono- or N,N-di-lower alkyl-carbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-, di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino-lower alkoxy, cyano-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy or together with $R^4$ is lower alkylenedioxy or a fused-on benzo or cyclohexeno ring, $R^4$ together with $R^3$ is lower alkylenedioxy or a fused-on benzo or cyclohexeno ring, or is hydrogen, lower alkyl, hydroxy, lower alkoxy or cycloalkoxy, X is methylene or hydroxymethylene, $R^5$ is lower alkyl or cycloalkyl, $R^6$ is amino, lower alkylamino, di-lower alkylamino or lower alkanoylamino, $R^7$ is lower alkyl, lower alkenyl, cycloalkyl, or phenyl- or naphthyl-lower alkyl that is unsubstituted or mono-, di- or tri-substituted by lower alkyl, lower alkoxy, hydroxy, lower alkylamino, di-lower alkylamino, halogen and/or by trifluoromethyl, and $R^8$ is lower alkyl, cycloalkyl, hydroxy-lower alkyl, lower alkanoyloxy-lower alkyl, lower alkoxy-lower alkyl or lower alkenyloxy-lower alkyl, amino-lower alkyl, lower alkanoyl-amino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxypiperidino-lower alkyl, piperazino-, N-lower alkylpiperazino- or N'-lower alkanoylpiperazino-lower alkyl, unsubstituted or lower alkylated morpholino-lower alkyl, such as morpholino-lower alkyl or dimethylmorpholino-lower alkyl, or optionally S-oxidised thiomorpholino-lower alkyl, such as thiomorpholino-lower alkyl, S,S-dioxothiomorpholino-lower alkyl, carboxy-lower alkyl, lower alkoxycarbonyl-lower alkyl, carbamoyl-lower alkyl, N-mono- or N,N-di-lower alkylcarbamoyl-lower alkyl, dicarboxy-lower alkyl, di-lower alkoxycarbonyl-lower alkyl, dicarbamoyl-lower alkyl, di-(N-mono- or N,N-di-lower alkylcarbamoyl)-lower alkyl, carboxy-(hydroxy)-lower alkyl, lower alkoxy-carbonyl-(hydroxy)-lower alkyl or carbamoyl-(hydroxy)-lower alkyl, cyano-lower alkyl, lower alkanesulfonyl-lower alkyl, sulfamoyl-lower alkyl, lower alkyl-sulfamoyl-lower alkyl, di-lower alkylsulfamoyl-lower alkyl, thiocarbamoyl-lower alkyl, lower alkylthiocarbamoyl-lower alkyl, di-lower alkylthiocarbamoyl-lower alkyl, pyrrolidinyl, imidazolyl, benzimidazolyl, oxadiazolyl, pyridyl, oxopiperidinyl, quinolinyl, unsubstituted or N-lower alkanoylated piperidyl or pyrrolidinyl, imidazolyl-lower alkyl, benzimidazolyl-lower alkyl, oxadiazolyl-lower alkyl, pyridyl-lower alkyl, unsubstituted or N-lower alkanoylated piperidyl-lower alkyl or pyrrolidinyl-lower alkyl, oxopiperidinyl-lower alkyl, quinolinyl-lower alkyl, morpholino-carbonyl-lower alkyl or unsubstituted or N-lower alkanoylated piperidyl-lower alkyl, and the salts thereof.

The invention relates especially to making compounds of formula (I) wherein $R^1$ is hydrogen, $R^2$ is lower alkyl, lower alkoxy-lower alkyl, lower alkoxy-lower alkoxy, lower alkoxy-lower alkoxy-lower alkyl; phenyl-lower alkoxy that is unsubstituted or substituted by lower alkyl, lower alkoxy, hydroxy, halogen, nitro and/or by amino; optionally N-oxidised pyridyl-lower alkoxy, lower alkylthio-lower alkoxy, lower alkane-sulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R^3$ is hydrogen, lower alkyl, hydroxy, lower alkoxy or polyhalo-lower alkoxy or together with $R^4$ is lower alkylenedioxy, $R^4$ is hydrogen or together with $R^3$ is lower alkylidenedioxy, X is methylene or hydroxymethylene, R⁵ is lower alkyl or cycloalkyl, R⁶ is amino, lower alkylamino, di-lower alkylamino or lower alkanoylamino, R⁷ is lower alkyl, and R⁸ is lower alkyl, hydroxy-lower alkyl, lower alkanoyl-lower alkyl, lower alkoxy-lower alkyl, lower alkenyloxy-lower alkyl, amino-lower alkyl, lower alkanoylamino-lower alkyl, such as 2-($C_1$-$C_4$ alkanoylamino)-2-methyl-propyl, such as 2-acetylamino-2-methyl-propyl or 2-formylamino-2-methyl-propyl, N-mono- or N,N-di-lower alkylamino-lower alkyl, piperidino-lower alkyl, hydroxypiperidino-lower alkyl, lower alkoxypiperidino-lower alkyl, morpholino-lower alkyl, dimethylmorpholino-lower alkyl, thiomorpholino-lower alkyl, S,S-dioxothiomorpholino-lower alkyl, carboxy-lower alkyl, lower alkoxycarbonyl-lower alkyl, carbamoyl-lower alkyl, N-mono- or N,N-di-lower alkylcarbamoyl-lower alkyl, carboxy-(hydroxy)-lower alkyl, lower alkoxycarbonyl-(hydroxy)-lower alkyl, carbamoyl-(hydroxy)-lower alkyl, 5- or 6-membered carboxycycloalkyl-lower alkyl, 5- or 6-membered lower alkoxycarbonyl-cycloalkyl-lower alkyl, 5- or 6-membered carbamoylcycloalkyl-lower alkyl, 5- or 6-membered N-mono- or N,N-di-lower alkylcarbamoylcycloalkyl-lower alkyl, cyano-lower alkyl, lower alkanesulfonyl-lower alkyl, sulfamoyl-lower alkyl, lower alkylsulfamoyl-lower alkyl, or di-lower alkylsulfamoyl-lower alkyl, imidazolyl-lower alkyl, oxopyrrolidinyl-lower alkyl, benzimidazolyl-lower alkyl, oxadiazolyl-lower alkyl, pyridyl-lower alkyl, oxopiperidinyl-lower alkyl or quinolinyl-lower alkyl, piperidin-4-yl-lower alkyl or 1-$C_1$-$C_7$-lower alkanoylpiperidin-4-yl-lower alkyl, and the salts thereof.

The invention relates above all to making compounds of formula (I) wherein

R¹ and R⁴ are hydrogen,

R² is $C_1$-$C_4$ alkoxy-$C_1$-$C_4$ alkoxy, such as 3-methoxypropyloxy, or $C_1$-$C_4$ alkoxy-$C_1$-$C_4$ alkyl, such as 4-methoxybutyl, R³ is $C_1$-$C_4$ alkyl, such as isopropyl or tert-butyl, or $C_1$-$C_4$ alkoxy, such as methoxy, R⁶ is amino, X is methylene, R⁵ and R⁷ are branched $C_1$-$C_4$ alkyl, such as isopropyl, and R⁸ is carbamoyl-$C_1$-$C_4$ alkyl, such as 2- or 3-carbamoylpropyl, 2-(3-carbamoyl)propyl or 1-(2-carbamoyl-2-methyl) propyl, N—$C_1$-$C_4$ alkylcarbamoyl-$C_1$-$C_4$ alkyl, such as 3-(N-methylcarbamoyl)propyl, 1-(N-methylcarbamoyl)prop-2-yl, 2-(N-methyl-carbamoyl)prop-1-yl, especially (2R)—(N-methylcarbamoyl)prop-1-yl, N,N-di-$C_1$-$C_4$ alkylcarbamoyl-$C_1$-$C_4$alkyl, such as N,N-dimethylcarbamoylmethyl or 2-(N,N-dimethylcarbamoyl)ethyl, 3-(N,N-dimethylcarbamoyl)propyl, morpholino-$C_1$-$C_4$ alkyl, such as 2-morpholinoethyl, 3-morpholinopropyl or 1-(2-morpholino-2-methyl)propyl, thiomorpholino-$C_1$-$C_4$ alkyl, such as 2-thiomorpholinoethyl, 4-(1-$C_1$-$C_4$ alkanoylpiperidyl)-$C_1$-$C_4$ alkyl, such as 2-[4-(1-acetyl)piperidinyl]ethyl, 2-oxopyrrolidinyl-$C_1$-$C_4$ alkyl, such as 2-oxopyrrolidin-5(S)-ylmethyl or 2-oxopyrrolidin-5 (R)-ylmethyl, and the salts thereof.

Especially effective are those compounds of formula (I) wherein at least one, for example one, two, or preferably all four, of the asymmetric carbon atoms of the main chain have the stereochemical configuration shown in formula (Ia)

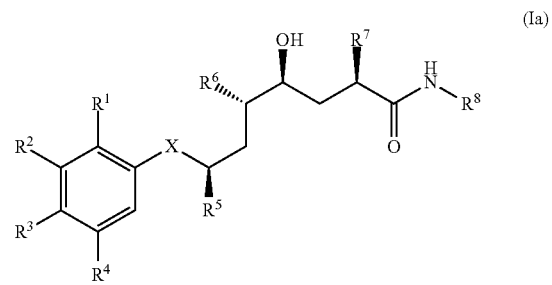

(Ia)

the variables each being as defined above, and the pharmaceutically acceptable salts thereof.

Accordingly, the invention relates preferably to making compounds of formula (I) wherein at least one, for example one, two, or preferably all four, of the asymmetric carbon atoms of the main chain have the stereochemical configuration shown in formula (Ia).

The invention relates very especially to the making of those of the above-defined compounds of formulae (I) and (Ia) that are described as being preferred wherein X is methylene.

The invention relates specifically to the making of the compounds of formula (I) mentioned in the Examples and to the salts thereof, especially the pharmaceutically acceptable salts thereof.

Suitable lactone ring-containing compound and/or lactam ring-containing compound can comprise compounds that can have their lactone ring and/or lactam ring opened when reacted with amine and catalyst (either monocarboxylic acid catalyst or other catalyst) under the conditions described herein.

In one non-limiting embodiment the lactone ring-containing compound and/or lactam ring-containing compound can comprise lactone ring-containing compound and/or lactam ring-containing compound other than the intermediate compound to δ-amino-γ-hydroxy-ω-aryl-alkanoic acid amide described herein.

Some non-limiting examples of lactones include α-lactone, β-lactone, γ-lactone, δ-lactone, ε-lactone and ƒ-lactone. In one embodiment, the lactone ring-containing compound is at least one of γ-decanolactone, β-butyrolactone, δ-decanolactone, β-propiolactone, D-glucono-δ-lactone, ε-caprolactone, δ-caprolactone, γ-butyrolactone, γ-caprolactone, (4R, 4aS,7R,7aR)-4-((R)-2,2-dimethyl-1,3-dioxolan-4-yl)-7-methoxy-2,2-dimethyldihydro-4H-furo[3,2-d][1,3]dioxin-6 (4aH)-one, (3aR,6R,6aR)-6-((tert-butyldimethylsilyloxy) methyl)-2,2-dimethyldihydrofuro[3,4-d][1,3]dioxol-4 (3aH)-one, and (3aR,4S,5R,6aS)-4-((tert-butyldimethylsilyloxy)methyl)-5-((tetrahydro-2H-pyran-2-yloxy)methyl)hexahydro-2H-cyclopenta[b]furan-2-one, and combinations thereof.

In another embodiment the intermediate compound to δ-amino-γ-hydroxy-ω-aryl-alkanoic acid amide is of the general formula (IV):

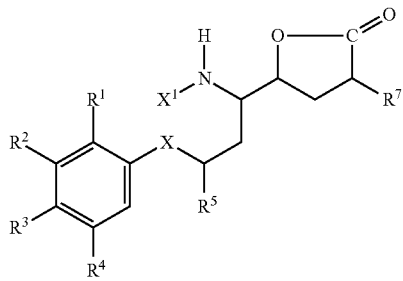

(IV)

wherein $R^1$, $R^2$, $R^3$, $R^4$, $R^5$, $R^7$, and X are as defined and $X^1$ is an amino-protecting group.

A preferred variant of that process is carried out by reacting, as the activated ester, an internal ester (γ-lactone) derived from the carboxylic acid of formula (I) and having the formula (IV), wherein X is methylene, with the compound of formula (V) $H_2N$—$R^*$ as described below, free functional groups present in the reactants, with the exception of the groups participating in the reaction, being if desired, as stated above, in protected form and any protecting groups being removed as described above. The opening of the lactone ring with the formation of the amide bond may be carried out under the conditions described herein, optionally in the presence of a suitable catalyst (either carboxylic acid or catalyst other than a carboxylic acid). In particular, a γ-lactone (IV) may be reacted with a primary amine of formula (V) $H_2N$—$R^*$ as described below, without a solvent or in the presence of a polar solvent, for example a lower alcohol, such as methanol or ethanol, an ether, such as tetrahydrofuran or dioxane, a nitrile, such as acetonitrile, an amide, such as dimethylformamide, N,N-dimethylacetamide, N-methyl-pyrrolidone or hexamethylphosphoric acid triamide, a urea, for example N,N'-dimethyl-N,N'-propylenylurea, a lower alkoxy-lower alkanol, for example diethylene glycol mono-methyl ether, in dimethyl sulfoxide or in a mixture of the mentioned solvents or in a mixture of one or more of the mentioned solvents with water, at temperatures of from room temperature to 150° C., preferably approximately from 20° C. to 100° C., and in the presence of a carboxylic acid catalyst or non-carboxylic acid catalyst such as 2-hydroxypyridine and/or triethylamine, the comments made herein applying in respect of the protecting groups.

The invention relates especially to processes that employ intermediate compounds of formula (IV) wherein at least one, for example one, two or preferably all, of the asymmetric carbon atoms of the main chain have the stereochemical configuration shown in formula (IVa)

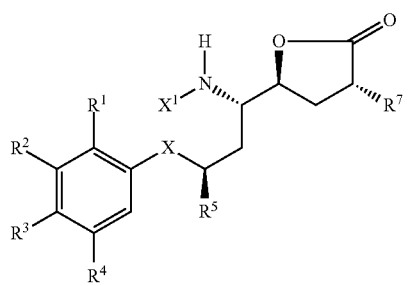

(IVa)

the variables each being as defined above, and the salts thereof.

The invention relates very especially to processes which employ intermediate compounds of formula (IVa) wherein
$R^1$ and $R^4$ are hydrogen,
$R^2$ is $C_1$-$C_4$ alkoxy-$C_1$-$C_4$ alkoxy, such as 3-methoxypropyloxy, or $C_1$-$C_4$ alkoxy-$C_1$-$C_4$-alkyl, such as 3-methoxybutyl,
$R^3$ is $C_1$-$C_4$ alkyl, such as isopropyl or tert-butyl, or $C_1$-$C_4$ alkoxy, such as methoxy,
X is methylene,
$R^5$ and $R^7$ are branched $C_1$-$C_4$ alkyl, such as isopropyl, and
$X^1$ is $C_1$-$C_7$ alkoxycarbonyl, such as tert-butoxycarbonyl,
and the salts thereof.

In yet a further embodiment there is provided an intermediate compound to the δ-amino-γ-hydroxy-ω-aryl-alkanoic acid amide of the general formula: (VI)

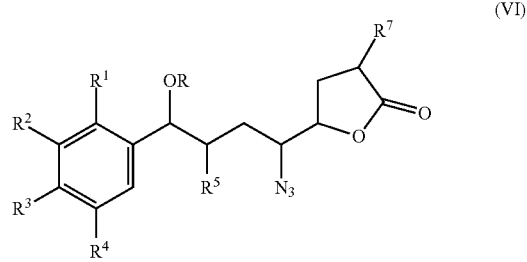

(VI)

wherein $R^1$, $R^2$, $R^3$, $R^4$, $R^5$ and $R^7$ as defined and the group-OR is a free or esterified or etherified hydroxyl group with R being a hydroxyl protecting group.

In one embodiment an intermediate compound to the δ-amino-γ-hydroxy-ω-aryl-alkanoic acid amide preferably can comprise 1,1-dimethylethyl[(1S,3S)-3-[[4-methoxy-3-(3-methoxypropoxy)phenyl]methyl]-4-methyl-1-[(2S,4S)-tetrahydro-4-(1-methylethyl)-5-oxo-2-furanyl]pentyl]carbamate.

Some non-limiting examples of lactams include α-lactam, β-lactam, γ-lactam, δ-lactam, ε-lactam and ƒ-lactam.

In one embodiment herein a lactone-ring containing and a lactam ring-containing compound can be of the general formula (A):

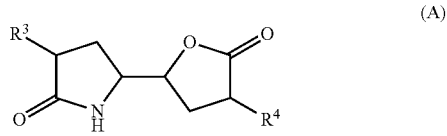

(A)

wherein
$R^3$ is $C_{1-7}$ alkyl or $C_{3-8}$ cycloalkyl; and $R^4$ is $C_{1-7}$ alkyl, $C_{2-7}$ alkenyl, $C_{3-8}$ cycloalkyl, phenyl- or naphthyl-$C_{1-4}$ alkyl each unsubstituted or mono-, di- or tri-substituted by $C_{1-4}$ alkyl, O—$C_{1-4}$ alkyl, OH, $C_{1-4}$ alkylamino, di-$C_{1-4}$ alkylamino, halogen and/or by trifluoromethyl; or a salt thereof. In one embodiment herein the lactone moiety of (A) could be first opened in the manner described herein followed by subsequent opening of the lactam in the same or different manner, or vice-versa, after which if desired, such a compound could be converted to aliskiren in the manner described herein or otherwise. U.S. Patent Publication No. 2008/0262246 which is physically appended hereto contains alternative processes for making aliskiren which are incorporated into the disclosure herein in their entirety and are considered part of the subject disclosure in its entirety.

In another embodiment herein a lactone-ring containing and a lactam ring-containing compound can be of the general formula (B):

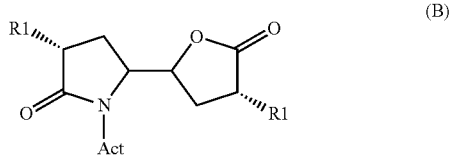

(B)

wherein each $R^1$ is independently of one another hydrogen; $C_{1-7}$ alkyl, $C_{3-8}$ cycloalkyl or benzyl, in particular both $R^1$ are branched $C_{3-6}$ alkyl such as isopropyl; and Act is an activating group selected from an amino protecting group; or a salt thereof.

In addition, any intermediates of compounds (A) or (B) described above, or compounds which are formed therefrom as intermediates for any renin inhibitor, which compounds contain a lactone ring and/or a lactam ring can be used as the lactone ring-containing and/or lactam ring-containing compound herein.

As stated above, any compound described herein, including lactone ring-containing and/or lactam ring-containing compound and intermediate compound to δ-amino-γ-hydroxy-ω-aryl-alkanoic acid amide can contain at least one protecting group.

A characteristic of protecting groups is that they can be removed readily (i.e. without the occurrence of undesired secondary reactions) for example by solvolysis, reduction, photolysis or alternatively under physiological conditions (e.g. by enzymatic cleavage). Different protecting groups can be selected so that they can be removed selectively at different steps while other protecting groups remain intact. The corresponding alternatives can be selected readily by the person skilled in the art.

It will be understood herein that the protecting group(s), as described herein, can be present on the lactone ring-containing and/or lactam ring-containing compound (or its salts) and on intermediate compound to δ-amino-γ-hydroxy-ω-aryl-alkanoic acid amide before the reaction with amine or, alternatively, can be removed prior to reaction with amine. In the event such protecting group(s) are not removed prior to reaction with amine, such protecting group(s) can be removed after such reaction with amine, for example, as described herein, in a conversion step (e.g., a deprotecting step) which may provide any one or more of a renin inhibitor intermediate, a renin inhibitor, or salts thereof. Protecting groups can be removed in any manner that is known to those skilled in the art which will not be described in detail herein in that such methods are well known to those skilled in the art, and such protecting groups can be removed in a manner as is described herein additionally or alternatively.

Functional groups in starting materials the reaction of which is to be avoided, especially carboxy, amino, hydroxy and mercapto groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example under physiological conditions. Protecting groups may also be present in the end products, however. Compounds of formula (I) having protected functional groups may have greater metabolic stability or pharmacodynamic properties that are better in some other way than the corresponding compounds having free functional groups.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H.-D. Jakubke and H. Jescheit, "Aminosauren, Peptide, Proteine" ("Amino acids, peptides, proteins"), Verlag Chemie, Weinheim, Deerfield Beach and Basle 1982, and in Jochen Lehmann, "Chemie der Kohlenhydrate: Monosaccharide and Derivate" ("The Chemistry of Carbohydrates: Monosaccharides and Derivatives"), Georg Thieme Verlag, Stuttgart 1974.

Amino-protecting groups $X^1$ are, for example, acyl groups other than lower alkanoyl, also arylmethyl, lower alkylthio, 2-acyl-lower alk-1-enyl or silyl. The group $X^1$—$N(X^2)$— can also be in the form of an azido group.

Acyl groups other than lower alkanoyl are, for example, halo-lower alkanoyl, for example 2-haloacetyl, such as 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, for example tertiary lower alkoxycarbonyl, such as tert-butoxycarbonyl, arylmethoxycarbonyl having one or two aryl radicals which are phenyl that is unsubstituted or mono- or poly-substituted, for example, by lower alkyl, for example tertiary lower alkyl, such as tertiary butyl, lower alkoxy, such as methoxy, hydroxy, halogen, such as chlorine, and/or by nitro, for example benzyloxycarbonyl, unsubstituted or substituted benzyloxycarbonyl, such as 4-nitrobenzyloxycarbonyl, diphenylmethoxycarbonyl, fluorenylmethoxycarbonyl or substituted diphenylmethoxycarbonyl, such as di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodo-ethoxycarbonyl, 2-(tri-substituted silyl)-lower alkoxycarbonyl, for example 2-tri-lower alkylsilyl-lower alkoxycarbonyl, for example 2-trimethylsilylethoxycarbonyl or 2-(di-n-butylmethyl-silyl)-ethoxycarbonyl, or triarylsilyl-lower alkoxycarbonyl, for example 2-triphenylsilylethoxycarbonyl.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tertiary butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or lower alkoxycarbonyl-prop-1-en-2-yl, for example 1-ethoxy-carbonyl-prop-1-en-2-yl.

A silylamino group is, for example, a tri-lower alkylsilylamino group, for example trimethylsilylamino. The silicon atom of the silylamino group can also be substituted by only two lower alkyl groups, for example methyl groups, and by the amino group or carboxy group of a second molecule of formula (I). Compounds having such protecting groups can be prepared, for example, using dimethylchlorosilane as silylating agent.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups $X^1$ are acyl radicals of carbonic acid semiesters, such as lower alkoxycarbonyl, especially tert-butyloxycarbonyl or fluorenylmethoxycarbonyl, unsubstituted or lower alkyl-, lower alkoxy-, nitro- and/or halo-substituted α-phenyl- or α,α-diphenyl-lower alkoxycarbonyl, such as benzyloxycarbonyl, p-nitrobenzyloxycarbonyl or diphenylmethoxycarbonyl, or 2-halo-lower alkoxycarbonyl, e.g. 2,2,2-trichloroethoxycarbonyl, also trityl or formyl.

Hydroxy-protecting groups $X^3$ are, for example, acyl groups, for example lower alkanoyl that is substituted by halogen, such as chlorine, for example 2,2-dichloroacetyl, or especially acyl radicals of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A further suitable hydroxy-protecting group $X^3$ is tri-lower alkylsilyl, for example trimethylsilyl, triisopropylsilyl or dimethyl-tert-butylsilyl, a readily removable etherifying group, for example an alkyl group, such as tertiary lower alkyl, for example tertiary butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, for example 2-tetrahydrofuryl or 2-tetrahydropyranyl, or a corresponding thia analogue, and also 1-phenyl-lower alkyl, for example benzyl, diphenylmethyl or trityl, wherein the phenyl radicals can be substituted, for example, by halogen, for example chlorine, lower alkoxy, for example methoxy, and/or by nitro.

Bivalent protecting groups formed by $X^2$ and $X^3$ together are, for example, methylene groups substituted by one or two alkyl radicals and are accordingly unsubstituted or substituted alkylidene, such as lower alkylidene, for example isopropylidene, cycloalkylidene, such as cyclohexylidene, also carbonyl or benzylidene.

If $X^4$ is reactively etherified or esterified hydroxy, the terminal group —(=O)—$X^4$ is a reactively functionally modified carboxylic acid function and is, for example, in the form of an activated ester or anhydride. The reactive acid derivatives can also be formed in situ.

The amido nitrogen of any amides described herein can also be protected if desired and the protecting group then be removed in the corresponding protected compound, or a salt thereof. This process step as such also forms an embodiment of the invention.

In another embodiment herein it will be understood that any amine can be employed for reaction with the lactone ring-containing and/or lactam ring-containing compound. Suitable non-limiting examples of such amine can comprise any amine that can react with a lactone ring-containing and/or lactam ring-containing compound and an intermediate compound to δ-amino-γ-hydroxy-ω-aryl-alkanoic acid amide, as described herein, in an aminolysis reaction.

Some suitable non-limiting examples of amines can comprise unsubstituted or hydroxy-substituted mono-, di- or tri-alkylamines, especially mono-, di- or tri-lower alkylamines, or for example methyl-, ethyl-, diethyl- or triethyl-amine, mono-, his- or tris-(2-hydroxy-lower alkyl)-amines, such as ethanol-, diethanol- or triethanol-amine, tris-(hydroxymethyl)-methylamine or 2-hydroxy-tert-butylamines, N,N-di-lower alkyl-N-(hydroxy-lower alkyl)-amines, such as N,N-dimethyl-N-(2-hydroxyethyl)-amine, or N-methyl-D-glucamine.

In one embodiment the amine can comprise tertiary amines including N tri-substituted ($C_{1-7}$ alkyl; $C_{3-8}$ cycloalkyl, phenyl, and/or phenyl-$C_{1-4}$ alkyl) amines such as the non-limiting examples of trimethylamine, DBU, triethylamine, diisopropylethylamine, ethyldiisopropylamine, pyridine, N-methylmorpholine or 4-dimethylaminopyridine.

Preferably, the amine is at least one of a primary amine and a secondary amine. More preferably the amine is a primary amine of the general formula (V) $H_2N$—R*, wherein R* is as defined for $R^8$, i.e., lower alkyl, cycloalkyl, free or aliphatically esterified or etherified hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, or a salt thereof.

The expression, "lower alkylene" herein can comprise an alkylene group having up to about 8 carbon atoms and preferably up to about 6 carbon atoms. Lower alkanoyloxy can also comprise from 1 to about 8, preferably from 1 to about 6 carbon atoms as can the term "lower" when used in conjunction with "alkylated thiocarbamoyl" and "alkylated sulfamoyl" herein.

Examples of primary amines include $C_{3-8}$ cycloalkylamines such as cyclohexylamine, primary aromatic amines, such as aniline, aryl alkyl amines such as benzylamine and including aryl branched alkyl amines such as phenyl- or naphthylethylamine. Secondary amines include N di-substituted ($C_{1-7}$ alkyl, $C_{3-8}$ cycloalkyl, phenyl, and/or phenyl-$C_{1-4}$ alkyl) amines such as di($C_{1-7}$ alkyl) amines or dicyclohexylamine.

One preferable examples of amine can comprise amine of the formula (VII):

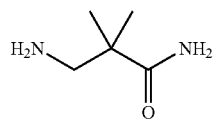

(VII)

The carboxylic acid that can be used herein can comprise any such acid which can effect lactone ring-opening and/or lactam ring-opening to provide ring-opened product(s) which then react with amine to provide final amide product(s). Preferably the carboxylic acid contains from 6 to about 30 carbon atoms, more preferably from about 6 to about 20 carbon atoms and most preferably from about 6 to about 18 carbon atoms. Lower end points to said ranges of carbon atoms for the carboxylic acid can also comprise 8, 10 and 12 carbon atoms.

Preferably, the carboxylic acid is a monocarboxylic acid of the general formula RCOOH wherein R is an organic, optionally halogenated, group; more preferably, wherein the organic group is selected from the group consisting of alkyl, cycloalkyl, alkenyl, aryl, substituted aryl, and aralkyl. Suitable alkyl groups for R can be selected from the group consisting of methyl, trichloromethyl, ethyl, propyl, isopropyl, n-butyl, sec-butyl, tert-butyl, n-pentyl, isopentyl, hexyl, 2-ethylhexyl, isohexyl, cyclohexyl, heptyl, 3-heptyl, 4-heptyl, isoheptyl, cycloheptyl, neoheptyl; n-octyl; 2-octyl; 3-octyl; 4-octyl; isooctyl; neooctyl; n-nonyl; 2-nonyl; 3-nonyl; 4-nonyl; 5-nonyl; isononyl; neononyl, and n-decyl, undecyl, dodecyl, tridecyl, eicosyl, henicosyl, triacontyl, and the like. Preferable alkyl groups for R can be selected from the group consisting of branched alkyl of 6-8 carbon atoms. In one embodiment, alkyl groups for R can be selected from the group consisting of 2-hexyl, 3-hexyl, 3-heptyl, 4-heptyl, 3-octyl, 4-octyl, and 5-octyl.

Suitable monocarboxylic acids in which R is saturated include 2-ethylhexanoic acid, 2-propylpentanoic acid, octanoic acid and trichloroacetic acid.

When the R group of the monocarboxylic acid formula above is cycloalkyl, such cycloalkyl can be selected from the group consisting of cyclopropyl, cyclobutyl, cyclopentyl, cyclohexyl and cycloheptyl. Suitable cyclic monocarboxylic acids include cyclopentanoic acid and cyclohexanecarboxylic acid (cyclohexanoic acid).

Suitable monocarboxylic acids include those in which R is unsaturated, e.g., butenyl, isobutenyl, pentenyl, isopentenyl, hexenyl, isohexenyl, etc. Suitable unsaturated monocarboxylic acids include tiglic acid ((E)-2-methylbut-2-enoic) acid) and 5-hexenoic acid.

When the R group of the monocarboxylic acid is aryl or substituted aryl, such group can be phenyl, methoxyphenyl, amine-substituted phenyl, halogen-substituted phenyl, and the like. Examples of suitable aryl and substituted-aryl carboxyclic acids include benzoic acid, o-anisoic acid (2-methoxybenzoic acid), trimethylaminobenzoic acid, 2-methoxybenzoic acid, 3-methoxybenzoic acid, 2-methylbenzoic acid, 3-methylbenzoic acid, 3-iodobenzoic acid, 3-chlorobenzoic acid, f-trifluoromethylbenzoic acid, f-nitrobenzoic acid and the like.

Polycarboxylic acids are also suitable for use as ring-opening catalysts herein. Included among the useful polycarboxylic acids are dicarboxylic acids such as fumaric acid, malic acid and tartaric acid.

The condensation to form an amide bond can be carried out in one non-limiting embodiment, in a manner known per se, for example as described in standard works, such as Houben-Weyl, "Methoden der organischen Chemie", 4th edition, Volume 15/II (1974), Volume IX (1955), Volume E 11 (1985), Georg Thieme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984, with the understanding that such condensations to form an amide bond may also in one other non-limiting embodiment be conducted in the presence of the recited carboxylic acid catalyst.

In one non-limiting embodiment, the condensation can be carried out in accordance with the technique known as solid-phase synthesis which originates from R. Merrifield and is described, for example, in Angew. Chem. 97, 801-812 (1985), Naturwissenschaften 71, 252-258 (1984) or in R. A. Houghten, Proc. Natl. Acad. Sci. U.S.A. 82, 5131-5135 (1985).

In one non-limiting embodiment the reaction of lactone ring-containing and/or lactam ring-containing compound or the intermediate compound to δ-amino-γ-hydroxy-ω-aryl-alkanoic acid amide, and amine can be conducted in the presence of a catalyst other than a carboxylic acid catalyst. Some examples of such catalysts other than carboxylic acid catalysts include metal salts, e.g., sodium 2-ethylhexanoate; triethylamine; 2-hydroxypyridine; organic and inorganic acids; and combinations thereof. In such an embodiment, the ring-opened product, i.e., the reaction product of the lactone ring-containing and/or lactam ring-containing compound or intermediate compound to δ-amino-γ-hydroxy-ω-aryl-alkanoic acid amide, and amine in the presence of such a catalyst, can be subjected to the conversion described herein, and specifically, can be subjected to deprotection of at least one protecting group as described herein.

In one embodiment herein the reaction between lactone ring-containing and/or lactam ring-containing compound or intermediate compound to δ-amino-γ-hydroxy-ω-aryl-alkanoic acid amide, and amine in the presence of carboxylic acid can be conducted under conditions sufficient to provide for the opening of the lactone ring and/or lactam ring. The conditions for ring-opening can vary depending on the specific reactants and catalyst chosen and can be adjusted accordingly, and as described herein. For example, such conditions for ring-opening can comprise the molar amounts, temperatures, and time periods, inter alia, described herein.

With regard to the reaction between lactone ring-containing and/or lactam ring-containing compound or intermediate compound to δ-amino-γ-hydroxy-ω-aryl-alkanoic acid amide, and amine in the presence of carboxylic acid, such ring-opening can be conducted in the absence of solvent, e.g., in the molten state, although, optionally solvent as described herein may be used in amounts of from about 0.1 M to about 2 M, preferably, 0.5 M to about 1.5 M, preferably from about 0.9 M to about 1.1 M.

The temperature of the reaction between lactone ring-containing and/or lactam ring-containing compound or intermediate compound to δ-amino-γ-hydroxy-ω-aryl-alkanoic acid amide, and amine in the presence of carboxylic acid can be from about 20° C. to about 140° C., preferably from about 70° C. to about 130° C. and most preferably from about 100° C. to about 120° C. In yet another embodiment herein the reaction between lactone ring-containing and/or lactam ring-containing compound or intermediate compound to δ-amino-γ-hydroxy-ω-aryl-alkanoic acid amide, and amine in the presence of carboxylic acid can be from about 90° C. to about 125° C., preferably from about 115° C. to about 125° C. and most preferably from about 118° C. to about 122° C.

Surprisingly, it has been found that by utilizing amounts of the carboxylic acid catalyst described herein in amount of from about 0.5 equivalents to about 1.5 equivalents to the molar amount of lactone employed, a molar excess of catalyst is not necessitated to provide for reaction equilibrium. Even more surprisingly, a catalyst other than an carboxylic acid catalyst, e.g., a metal salt catalyst, is not required and the reaction of lactone ring-containing and/or lactam ring-containing compound or intermediate compound to δ-amino-γ-hydroxy-ω-aryl-alkanoic acid amide, and amine can proceed in the absence of a metal salt catalyst, such as, for example, in the absence of sodium 2-ethylhexanoate. Preferably, the amount of carboxylic acid catalyst can be from about 0.6 to about 1.4 equivalents to the molar amount of lactone ring-containing and/or lactam ring-containing compound or intermediate compound to δ-amino-γ-hydroxy-ω-aryl-alkanoic acid amide employed, more preferably from about 0.8 to about 1.2 equivalents to the molar amount of lactone ring-containing and/or lactam ring-containing compound or intermediate compound to δ-amino-γ-hydroxy-ω-aryl-alkanoic acid amide employed, and most preferably from about 0.9 to about 1.1 equivalents to the molar amount of lactone ring-containing and/or lactam ring-containing compound or intermediate compound to δ-amino-γ-hydroxy-ω-aryl-alkanoic acid amide employed.

The amount of amine employed in the reaction between lactone ring-containing and/or lactam ring-containing compound or intermediate compound to δ-amino-γ-hydroxy-ω-aryl-alkanoic acid amide, and amine in the presence of carboxylic acid can be from about 1 to about 50, preferably from about 2 to about 35 and most preferably from about 3 to about 20 molar equivalents based on the amount of lactone ring-containing and/or lactam ring-containing compound or intermediate compound to δ-amino-γ-hydroxy-ω-aryl-alkanoic acid amide employed.

With regard to the reaction between lactone ring-containing and/or lactam ring-containing compound or intermediate compound to δ-amino-γ-hydroxy-ω-aryl-alkanoic acid amide, and amine in the presence of catalyst other than carboxylic acid, such ring-opening can be conducted in the same reaction conditions indicated herein for the use of carboxylic acid catalyst, with the exception that the amount of catalyst in the process that employs catalyst other than carboxylic acid catalyst is from about 0.5 equivalents to about 2 equivalents, preferably from about 0.9 to about 1.6 and most preferably from about 1.1 to about 1.4 molar equivalents of catalyst based on the equivalents of molar amount of lactone ring-containing and/or lactam ring-containing compound or intermediate compound to δ-amino-γ-hydroxy-ω-aryl-alkanoic acid amide employed.

The reaction between lactone ring-containing and/or lactam ring-containing compound or intermediate compound to δ-amino-γ-hydroxy-ω-aryl-alkanoic acid amide, and amine in the presence of carboxylic acid can proceed for a period as deemed necessary to obtain the desired level of ring-opened product, which can vary depending on reaction conditions and the specific components employed. Desired levels of reaction can comprise greater than 70% conversion to ring opened product, preferably greater than 80% conversion to ring opened product and most preferably greater than 90% conversion to ring opened product, with such percentages being based on the molar amount of reactant lactone ring-containing and/or lactam ring-containing compound, or intermediate compound to δ-amino-γ-hydroxy-ω-aryl-alkanoic acid amide.

In one embodiment, surprisingly, the time period for such reaction between lactone ring-containing and/or lactam ring-containing compound or intermediate compound to δ-amino-γ-hydroxy-ω-aryl-alkanoic acid amide, and amine in the presence of carboxylic acid to the above desired levels of conversion to ring-opened product can proceed from about 5 minutes to about 12 hours, preferably from about 10 minutes to about 6 hours and most preferably from about 20 minutes to about one and a half hours. In one preferable embodiment, the time period for such reaction between lactone ring-containing and/or lactam ring-containing compound or intermediate compound to δ-amino-γ-hydroxy-ω-aryl-alkanoic acid amide and amine in the presence of monocarboxylic acid to the above desired levels of conversion to ring-opened product can proceed from about 40 minutes to about 3 hours.

In another embodiment, the time period for such reaction between lactone ring-containing and/or lactam ring-containing compound or intermediate compound to δ-amino-γ-hydroxy-ω-aryl-alkanoic acid amide, and amine in the presence of carboxylic acid to the above desired levels of conversion to ring-opened product can proceed in a time period that is greater than 10 fold less in duration than an equivalent reaction that employs metal salt catalyst, preferably, is greater than 20 fold less in duration than an equivalent reaction that employs metal salt catalyst, and most preferably is greater than 50 fold less in duration than an equivalent reaction that employs metal salt catalyst. The expression "other than carboxylic acid" as referring to the catalyst, can be equivalent to a metal salt catalyst and vice-versa, or can comprise a class containing metal salt catalyst, inter alia, such as for example, the metal salt catalyst described herein, e.g., sodium 2-ethylhexanoate.

In one specific embodiment herein, the conditions sufficient to provide for the opening of the lactone and/or lactam ring comprise reacting at a temperature of from about 80° C. to about 160° C. for a period of from about 5 minutes to about 5 hours.

The reaction product of the reaction of lactone ring-containing and/or lactam ring-containing compound or intermediate compound to δ-amino-γ-hydroxy-ω-aryl-alkanoic acid amide, and amine in the presence of carboxylic acid (ring-opened product), can be an δ-amino-γ-hydroxy-ω-aryl-alkanoic acid amide in and of itself (or salts thereof), such as for example, aliskiren, or can be an intermediate which can be converted to δ-amino-γ-hydroxy-ω-aryl-alkanoic acid amide (or salts thereof) such as for example, aliskiren.

Prior to conversion of the ring-opened product to a desired product (such as aliskiren or its salt(s)) the ring-opened product reaction mixture can be subject to separation of the ring-opened product by means known in the art, e.g., partitioning between a suitable solvent, e.g., isopropyl acetate or ethyl acetate, inter alia, and water and the layers separated. The separated ring-opened product can then be crystallized from the separated organic phase by means known in the art.

In one non-limiting embodiment, conversion of the ring-opened product can comprise any intermediate synthesis step(s) that are known to those skilled in the art and will depend on the ring-opened product and the desired product, e.g., a specific renin inhibitor, such as aliskiren.

Such conversion of the ring-opened product can comprise, among other optional steps, removing any protecting group(s) as described herein in a deprotection step following the reaction between lactone ring-containing and/or lactam ring-containing compound, or intermediate compound to δ-amino-γ-hydroxy-ω-aryl-alkanoic acid amide, and amine in the presence of carboxylic acid (or alternatively in the presence of a catalyst other than carboxylic acid catalyst, e.g., metal salt catalyst).

In addition to, or alternatively to a deprotection step, conversion of the ring-opened product can comprise removing any activating group(s) (Act), and if desired, converting the ring-opened product, i.e., an obtainable free compound or an obtainable salt, into a salt or a free compound, respectively. Conversion to a salt can also comprise converting a salt to a different salt thereof. In addition, or alternatively, such removal of activating groups or conversion can occur prior to the reaction between lactone ring-containing and/or lactam ring-containing compound or intermediate compound to δ-amino-γ-hydroxy-ω-aryl-alkanoic acid amide, and amine.

(Act) as used herein is an activating group selected from a protecting group such as the non-limiting examples of an amino protecting group, in particular a carbamate, or a salt thereof. The activating group may be introduced at a nitrogen of any lactone ring-containing and/or lactam ring-containing compound or intermediate compound to δ-amino-γ-hydroxy-ω-aryl-alkanoic acid amide described herein, or to precursors to any one or more thereof.

Conversion of the ring-opened product can further, or alternatively, comprise (i) freeing a hydroxymethyl group from a group —OR, wherein —OR is a free or esterified or etherified hydroxyl group with R being a hydroxyl protecting group directly bound to the main chain of the ring-opened reaction product, or replacing such group —OR reductively by hydrogen; or (ii) reducing an azido group, which is bound to the main chain of the ring-opened reaction product, to amino with hydrogen.

In one non-limiting embodiment, conversion of the ring-opened product can comprise deprotection of any protecting group(s), such as the non-limiting examples of azide, amino protecting groups, and hydroxyl protecting groups. As stated herein, such deprotection can additionally or alternatively occur prior to reaction between lactone ring-containing and/or lactam ring-containing compound or intermediate compound to δ-amino-γ-hydroxy-ω-aryl-alkanoic acid amide, and amine (regardless of whether carboxylic acid catalyst or catalyst other than carboxylic acid catalyst is employed).

It will be understood herein that when catalyst other than carboxylic acid catalyst is employed in the reaction between lactone ring-containing and/or lactam ring-containing compound or intermediate compound to δ-amino-γ-hydroxy-ω-aryl-alkanoic acid amide, and amine that at least one deprotection step will occur, prior to and/or after such reaction employing aqueous halogenic acid.

Deprotection, as described herein, can comprise contacting the ring-opened product (either separated or in reaction mixture) and/or the lactone ring-containing and/or lactam ring-containing compound, or intermediate compound to δ-amino-γ-hydroxy-ω-aryl-alkanoic acid amide with aqueous acid, preferably, aqueous halogenic acid. In one non-limiting embodiment, aqueous halogenic acid can comprise aqueous hydrochloric acid, preferably concentrated aqueous hydrochloric acid, aqueous hydrobromic acid, or trifluoroacetic acid or combinations thereof. Other aqueous acids can comprise sulfuric acids and any aqueous inorganic acid, Such contact of the ring-opened product and/or lactone ring-containing and/or lactam ring-containing compound, or intermediate compound to δ-amino-γ-hydroxy-ω-aryl-alkanoic acid amide with aqueous halogenic acid can in and of itself result in deprotection of at least one protecting group(s).

In one embodiment the ring-opened product and/or lactone ring-containing and/or lactam ring-containing compound or intermediate compound to δ-amino-γ-hydroxy-ω-aryl-alkanoic acid amide, is in contact with aqueous halogenic acid in the absence of gaseous halogenic acid, e.g., in the absence of, gaseous hydrochloric acid alone, or gaseous hydrochloric acid in diisopropyl ether.

As described above, the ring-opened product can be obtained using other than an carboxylic acid catalyst. In the embodiment wherein the ring-opened product is obtained using other than an carboxylic acid catalyst, such ring-opened product can be subjected to the same conversion step(s) described herein, e.g., the same deprotection step employing aqueous halogenic acid.

Optionally, the halogenic acid can be suspended in a solvent. The solvent can be selected from the group consisting of water, ester, alcohol, ether, cyclic ether, liquid aromatic hydrocarbon, nitrile, halogenated hydrocarbon, acid amide, heterocyclic nitrogen base, carboxylic acid anhydride, cyclic, linear or branched hydrocarbon; and, mixtures thereof.

Preferably, the solvent is selected from the group consisting of ethyl acetate, isopropyl acetate, tert-butyl acetate, THF, TBME, methanol, ethanol, 1-propanol, 2-propanol, dichloromethane, diethyl ether, dioxane, benzene, toluene, acetonitrile, chloroform, N,N-dimethylformamide, N,N-dimethyl acetamide, pyridine, N-methylpyrrolidin-2-one, acetic anhydride, cyclohexane, hexane, isopentane, diisopropyl ether and combinations thereof.

In one preferable embodiment herein following the reaction of lactone (IV) with amine (V) in the presence of carboxylic acid, the step of converting the reaction product comprises deprotecting the ring-opened reaction product by removing $X^1$ protecting group to produce δ-amino-γ-hydroxy-ω-aryl-alkanoic acid amide. As described above, deprotecting the reaction product can comprise employing aqueous halogenic acid, in solvent or in the absence of solvent.

In one other preferable embodiment herein following the reaction of lactone (VI) with amine (V) in the presence of carboxylic acid, the step of converting the reaction product comprises (i) freeing hydroxymethyl from the group —OR or replacing the group —OR reductively by hydrogen; (ii) reducing the azido group to amino with hydrogen; and, (iii) deprotecting any protecting groups present to produce δ-amino-γ-hydroxy-ω-aryl-alkanoic acid amide, wherein steps (i) and (ii) can be conducted in any order and/or simultaneously.

When employing formula (VI), in the reaction(s) described herein with (V), functional groups of (VI) that are not to participate in the reaction(s) are protected by one of the protecting groups mentioned herein. For example, wherein the group —OR is a free or esterified or etherified hydroxy group, with R preferably being a hydroxy-protecting group, such as especially isobutyryl. In such reaction(s) of (VI) with (V), R* of formula (V) has one of the meanings given under formula (I) for $R^8$, and, if desired such reaction, results in freeing hydroxymethyl from the group —OR or replacing the group —OR reductively by hydrogen.

Reducing agents suitable for the reduction of the azido group are those which under the reaction conditions of the process reduce an optionally functionalised hydroxy group or azido group selectively or more rapidly than the amide groups present in compounds of formula (I).

The reduction is preferably carried out with hydrogen in the presence of suitable heavy metal catalysts, for example Raney nickel or platinum or palladium catalysts, for example platinum or palladium on active carbon.

Most preferably, the solvent for the halogenic acid is ethyl acetate.

In one preferable, non-limiting embodiment, the step of contacting the ring-opened product (either separated or in reaction mixture), and/or lactone ring-containing and/or lactam ring-containing compound or intermediate compound to δ-amino-γ-hydroxy-ωaryl-alkanoic acid amide, with aqueous halogenic acid (without any solvent) can be conducted for a period of time from about 20 seconds to about 1 hour, preferably from about 30 seconds to about 30 minutes and most preferably from about 1 minute to about 10 minutes.

In another preferable, non-limiting embodiment, the step of contacting the ring-opened product (either separated or in reaction mixture) and/or lactone ring-containing and/or lactam ring-containing compound or intermediate compound to δ-amino-γ-hydroxy-ω-aryl-alkanoic acid amide, with aqueous halogenic acid (with solvent) can be conducted for a period of time from about 1 minute to about 1 hour, preferably from about 2 minutes to about 30 minutes and most preferably from about 5 minutes to about 10 minutes.

The temperature at which said ring-opened product (either separated or in reaction mixture), and/or lactone ring-containing and/or lactam ring-containing compound or intermediate compound to δ-amino-γ-hydroxy-ω-aryl-alkanoic acid amide, is contacted with aqueous halogenic acid (in solvent or not) can be from about 0 to about 50, preferably from about 10 to about 40 and most preferably from about 20 to about 30° C.

In one embodiment herein, the temperature at which said ring-opened product (either separated or in reaction mixture), and/or lactone ring-containing and/or lactam ring-containing compound or intermediate compound to δ-Amino-γ-hydroxy-ω-aryl-alkanoic acid amide, is contacted with aqueous halogenic acid (in solvent or not) can be from about 0° C. to about 50° C., preferably from about 10° C. to about 30° C. and most preferably from about 20° C. to about 25° C.

The amount of aqueous halogenic acid that can be contacted with the ring-opened product, and/or lactone ring-containing and/or lactam ring-containing compound or intermediate compound to δ-amino-γ-hydroxy-ω-aryl-alkanoic acid amide, can comprise from about 1 equivalent to about 30 equivalents, preferably from about 5 equivalents to about 20 equivalents and most preferably from about 8 equivalents to about 15 equivalents. In one non-limiting embodiment, a preferable amount of aqueous halogenic acid that can be contacted with the ring-opened product, and/or lactone ring-containing and/or lactam ring-containing compound or intermediate compound to δ-amino-γ-hydroxy-ω-aryl-alkanoic acid amide, can comprise about 12 equivalents.

Following contact of said ring-opened product with halogenic acid (in solvent or not) such can result in desired reaction product(s) (e.g., aliskiren and/or its salts) in conversion amounts of greater than 95%, preferably greater than 97% and most preferably greater than 99%, with such percents based on the amount of ring-opened product employed.

Further, following contact of said ring-opened product, and/or lactone ring-containing and/or lactam ring-containing compound or intermediate compound to δ-amino-γ-hydroxy-ω-aryl-alkanoic acid amide, with halogenic acid (in solvent or not) the reaction mixture containing the desired reaction product(s), and/or lactone ring-containing and/or lactam ring-containing compound or intermediate compound to δ-amino-γ-hydroxy-ω-aryl-alkanoic acid amide, can have any excess acid quenched with an appropriate base, e.g. NaOH and have the product, and/or lactone ring-containing and/or lactam ring-containing compound or intermediate compound to δ-amino-γ-hydroxy-ω-aryl-alkanoic acid amide, extracted with a suitable solvent, e.g., isopropyl acetate and/or ethyl acetate.

In one embodiment herein, the reaction of lactone ring-containing and/or lactam ring-containing compound or intermediate compound to δ-amino-γ-hydroxy-ω-aryl-alkanoic acid amide with amine, which is conducted in the absence of a metal salt (e.g., in the presence of only a carboxylic acid catalyst), can be completed to the same level of conversion as an equivalent process containing only a metal salt catalyst, but wherein the reaction time is at least half of the equivalent reaction, and further wherein the carboxylic acid is present in an amount of from about 1.50 equivalents to about 0.50 equivalents to the compound comprising a lactone-ring and/or a lactam ring or intermediate compound to δ-amino-γ-hydroxy-ω-aryl-alkanoic acid amide.

The removal of protecting groups that are not constituents of the desired end product of formula (I), for example carboxy-, amino-, hydroxy- and/or mercapto-protecting groups, which may be carried out subsequent to the process variants described above, is effected in a manner known per se, for example by means of solvolysis, especially hydrolysis, alcoholysis or acidolysis, or by means of reduction, especially hydrogenolysis or chemical reduction, as well as photolysis, as appropriate stepwise or simultaneously, it being possible also to use enzymatic methods. The removal of the protecting groups is described, for example, in the standard works mentioned hereinabove in the section relating to protecting groups.

For example, protected carboxy, for example tertiary lower alkoxycarbonyl, lower alkoxycarbonyl substituted in the 2-position by a trisubstituted silyl group or in the 1-position by lower alkoxy or by lower alkylthio, or unsubstituted or substituted diphenylmethoxycarbonyl can be converted into free carboxy by treatment with a suitable acid, such as formic acid or trifluoroacetic acid, where appropriate with the addition of a nucleophilic compound, such as phenol or anisole. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(H) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. 2-(Tri-substituted silyl)-lower alkoxycarbonyl, such as 2-tri-lower alkylsilyl-lower alkoxycarbonyl, can be converted into free carboxy also by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as tetralower alkyl-ammonium fluoride or tri-lower alkylarylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases.

A protected amino group is freed in a manner known per se and, according to the nature of the protecting groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-(tri-substituted silyl)-lower alkoxycarbonylamino, such as 2-tri-lower alkylsilyl-lower alkoxycarbonylamino, can be cleaved by treatment with a suitable acid, for example formic or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting condensation product. An amino group protected by 2-(tri-substituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. Likewise, silyl, such as trimethylsilyl, bonded directly to a hetero atom, such as nitrogen, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy or mercapto group protected by a suitable acyl group, by a tri-lower alkylsilyl group or by unsubstituted or substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group protected by tertiary lower alkyl or by a 2-oxa- or 2-thia-aliphatic or -cycloaliphatic hydrocarbon radical is removed by acidolysis, for example by treatment with a mineral acid or a strong carboxylic acid, for example trifluoroacetic acid. Mercapto protected by pyridyldiphenylmethyl can be freed, for example, using mercury(II) salts at pH 2-6 or by zinc/acetic acid or by electrolytic reduction; acetamidomethyl and isobutyrylamidomethyl can be removed, for example, by reaction with mercury(II) salts at pH 2-6; 2-chloroacetamidomethyl can be removed, for example, using 1-piperidinothiocarboxamide; and S-ethylthio, S-tert-butylthio and S-sulfo can be cleaved, for example, by thiolysis with thiophenol, thioglycolic acid, sodium thiophenolate or 1,4-dithiothreitol. Two hydroxy groups or an adjacent amino and hydroxy group which are protected together by means of a bivalent protecting group, preferably, for example, by a methylene group mono- or di-substituted by lower alkyl, such as lower alkylidene, for example isopropylidene, cyclo-alkylidene, for example cyclohexylidene, or benzylidene, can be freed by acid solvolysis, especially in the presence of a mineral acid or a strong organic acid. 2-Halo-lower alkoxycarbonyl is also removed using the above-mentioned reducing agents, for example a reducing metal, such as zinc, reducing metal salts, such as chromium(II) salts, or using sulfur compounds, for example sodium dithionite or preferably sodium sulfide and carbon disulfide.

When several protected functional groups are present, if desired the protecting groups may be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups may also be so selected that they are not all removed simultaneously, but rather they are removed in a desired sequence or only some of them are removed.

In one embodiment herein compounds of formula (VIII)

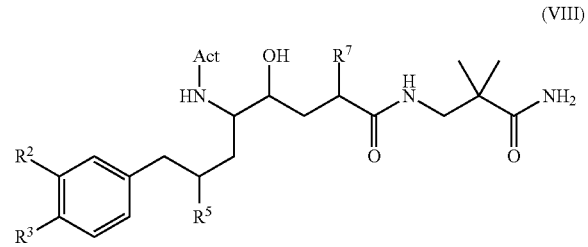

(VIII)

may be converted into a compound of formula (II) wherein $R^5$ and $R^7$ are as defined for a compound of formula (II), $R^2$ and $R^3$ are as defined for a compound of formula (II), or a salt thereof, said conversion comprising removing the activating group Act; and, if desired, converting an obtainable free compound of the formula VIII into a salt (which is preferred) or an obtainable salt into the free compound of the formula VIII or a different salt thereof. For example, if Act is (what is preferred) a $C_1$-$C_7$-alkoxycarbonyl group, such as tert-butoxycarbonyl, the removal can take place under customary conditions, e.g. in the presence of an acid, such as hydrohalic acid, in an appropriate solvent, such as dioxane, e.g. at temperatures from 0 to 50° C., for example at room temperature. The removal of the group Act is performed using standard protecting group chemistry following the procedures as described in the literature referenced herein or using methods well known in the art, see e.g. EP-A-0678 503, in particular example 130, and optionally salt formation using reaction conditions as described e.g. in U.S. Pat. No. 5,559, 111, see in particular example 83.

In each of the processes mentioned above, the compounds may also be used in the form of salts, provided that the reaction conditions allow it.

Compounds of formula (I) obtainable in accordance with the process can be converted into different compounds of formula I in customary manner.

For example, in a compound of formula (I) obtainable in accordance with the process, hydroxymethyl X can be reduced reductively to methylene, for example by catalytic hydrogenation in the presence of palladium-on-carbon.

Furthermore, in a compound of formula (I) obtainable in accordance with the process, a carboxy group in free or reactive form may be esterified or amidated or an esterified or amidated carboxy group may be converted into a free carboxy group.

For the esterification or amidation of a carboxy group in a compound of formula (I), if desired the free acid can be used or the free acid can be converted into one of the abovementioned reactive derivatives and reacted with an alcohol, with ammonia, or with a primary or secondary amine, or, in the case of esterification, the free acid or a reactive salt, for example the cesium salt, can be reacted with a reactive derivative of an alcohol. For example the cesium salt of a carboxylic acid can be reacted with a halide or sulfonic acid ester corresponding to the alcohol. The esterification of the carboxy group can also be carried out with other customary alkylating agents, for example with diazomethane, Meerwein salts or 1-substituted 3-aryltriazenes.

For the conversion of an esterified or amidated carboxy group into the free carboxy group it is possible to use one of the methods described above for the removal of carboxyprotecting groups or, if desired, alkaline hydrolysis in accordance with the reaction conditions mentioned in Organikum, 17th edition, VEB Deutscher Verlag der Wissenschaften, Berlin 1988.

In a compound of formula (I) obtainable in accordance with the process, an esterified carboxy group can be converted into an unsubstituted or substituted carboxamide group by aminolysis with ammonia or with a primary or secondary amine, optionally in the presence of a suitable condensation agent or catalyst. The aminolysis can be carried out in accordance with the reaction conditions mentioned for such reactions in Organikum, 15th edition, VEB Deutscher Verlag der Wissenschaften, Berlin (East) 1976.

A free amino group present in a compound of formula (I) obtainable in accordance with the process can be acylated or alkylated, for example to introduce a radical $R^6$ other than a primary amine. The acylation and the alkylation can be carried out in accordance with one of the methods mentioned for protecting groups or according to one of the processes mentioned in Organikum, 17th edition, VEB Deutscher Verlag der Wissenschaften, Berlin (East) 1988.

Furthermore, a free hydroxy group present in a compound of formula (I) obtainable in accordance with the process, for example as a constituent of the radical $R^8$, can be acylated. The acylation can be carried out with acylating reagents in accordance with one of the methods mentioned for protecting groups or according to one of the processes mentioned in Organikum, 17th edition, VEB Deutscher Verlag der Wissenschaften, Berlin (East) 1988.

In a compound of formula (I) obtainable in accordance with the process it is also possible to obtain from a sulfide the corresponding sulfoxide or sulfone, that is to say to oxidise a thio group to a sulfinyl or sulfonyl group or a sulfinyl group to sulfonyl, and also to oxidise thiomorpholino to S-oxy- or S,S-dioxy-thiomorpholino.

The oxidation to the sulfone can be carried out with most of the customary oxidising agents. It is especially preferable to use oxidising agents that oxidise the thio group or the sulfide sulfur selectively in the presence of other functional groups, for example amino or hydroxy groups, of the compound of formula (I) in question, for example aromatic or aliphatic peroxycarboxylic acids, for example peroxybenzoic acid, monoperphthalic acid, m-chloroperbenzoic acid, peracetic acid, performic acid or trifluoroperacetic acid. The oxidation with peroxycarboxylic acids is carried out in suitable solvents customarily used for that purpose, for example chlorinated hydrocarbons, for example methylene chloride or chloroform, ethers, such as diethyl ether, esters, such as ethyl acetate or the like, at temperatures of from −78° C. to room temperature, for example from −20° C. to +10° C., preferably about 0° C. The peroxycarboxylic acid can also be formed in situ, for example with hydrogen peroxide in acetic acid or formic acid that optionally contains acetic anhydride, for example with 30% or 90% hydrogen peroxide in acetic acid/acetic anhydride. Other peroxo compounds are also suitable, for example potassium peroxomonosulfate in lower alkanol/water mixtures, for example methanol/water or ethanol/water, or in aqueous acetic acid at temperatures of from −70° C. to +30° C., for example from −20° C. to room temperature, and also sodium metaperiodate in methanol or methanol/water mixtures at temperatures of from 0° C. to 50° C., for example about room temperature. If stoichiometric amounts of the mentioned oxidising agents are used it is also possible to obtain the corresponding sulfoxides.

If desired, it is possible by reduction of a sulfonyl group or a sulfone radical in an obtainable compound of formula (I) to obtain the corresponding thio compound or the corresponding sulfide, for example with diisobutylaluminum hydride in ether or tetrahydrofuran.

In compounds of formula (I) it is also possible to replace hydroxy $R^1$, $R^2$, $R^3$ and/or $R^4$ by one of the etherified hydroxy groups mentioned under formula (I) by reacting the corresponding compound of formula (I) wherein $R^1$, $R^2$, $R^3$ and/or $R^4$ is hydroxy in customary manner, for example in the presence of a basic condensation agent, with a compound of the formula (e) $R'^2$—Y, $R'^3$—Y and/or $R'^4$—Y wherein $R'^1$ is lower alkyl or free or esterified or amidated carboxy-lower alkyl, $R'^2$ is lower alkyl, lower alkoxy-lower alkyl, lower alkoxy-lower alkoxy-lower alkyl, cycloalkoxy-lower alkyl, optionally lower alkanoylated, halogenated or sulfonylated hydroxy-lower alkyl, oxo-lower alkyl, lower alkyl, lower alkenyl, cycloalkoxy-lower alkyl, lower alkoxy-lower alkyl, lower alkoxy-lower alkenyl, lower alkenyloxy-lower alkyl, lower alkenyloxy-lower alkyl, lower alkenyloxy-lower alkyl, lower alkanoyl-lower alkyl, optionally S-oxidised lower alkyl-thio-lower alkyl, lower alkylthio-(hydroxy)-lower alkyl, aryl-lower alkyl, optionally hydrogenated heteroaryl-lower alkyl, optionally hydrogenated heteroarylthio-lower alkyl, cyano-lower alkyl or free or esterified or amidated carboxy-lower alkyl, $R'^3$ is lower alkyl, lower alkoxy-lower alkyl, hydroxy-lower alkyl, aryl-lower alkyl, halogenated lower alkyl, cyano-lower alkyl or free or esterified or amidated carboxy-lower alkyl, and $R'^4$ is lower alkyl, and Y is reactive esterified hydroxy, especially hydroxy esterified by a mineral acid, by sulfuric acid or by an organic sulfonic acid, a halogen, preferably chlorine, bromine or iodine, groups of the formula O—SO$_2$—O—R'$_A$, or lower alkanesulfonyloxy or unsubstituted or substituted benzenesulfonyloxy, especially methane-, ethane-, benzene-, p-toluene- or p-bromobenzene-sulfonyl. R'$_A$ is defined as any alkyl or aryl containing from 1 to about 30 carbon atoms, especially p-nitrophenyl. The reaction is, as mentioned, preferably carried out in the presence of a basic condensation agent, such as an alkali metal carbonate, for example potassium carbonate, in an inert solvent, such as a lower alkanol, such as methanol, ethanol, butanol, tert-butanol or especially amyl alcohol, advantageously at elevated temperature, for example in a temperature range of approximately from 40° to 140° C., if necessary with removal of the resulting water of reaction by distillation, for example by azeotropic distillation.

It is also possible for salts of compounds of formula (I) obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula (I), including their salts, may also be obtained in the form of hydrates or may include the solvent used for crystallisation.

As a result of the close relationship between the compounds herein in free form and in the form of their salts, hereinabove and hereinbelow any reference to the free compounds and their salts is to be understood as including also the corresponding salts and free compounds, respectively, as appropriate and expedient.

Stereoisomeric mixtures, that is to say mixtures of diastereoisomers and/or enantiomers, such as, for example, racemic mixtures, can be separated into the corresponding isomers in a manner known per se by suitable separating processes. For example, mixtures of diastereoisomers can be separated into the individual diastereoisomers by fractional crystallisation, chromatography, solvent partition etc. Racemates can be separated from one another, after conversion of the optical antipodes into diastereoisomers, for example by reaction with optically active compounds, for example optically active acids or bases, by chromatography on column materials charged with optically active compounds or by enzymatic methods, for example by selective reaction of only one of the two enantiomers. This separation can be carried out either at the stage of one of the starting materials or with the compounds of formula (I) themselves.

In a compound of formula (I) the configuration at individual stereogenic centres can be selectively reversed. For example, the configuration of asymmetric carbon atoms that carry nucleophilic substituents, such as amino or hydroxy, can be reversed by second order nucleophilic substitution, optionally after conversion of the bonded nucleophilic substituent into a suitable nucleofugal leaving group and reaction with a reagent introducing the original substituent, or the configuration at carbon atoms having hydroxy groups can be reversed by oxidation and reduction, analogously to European Patent Application EP-A-0 236 734.

Also advantageous is the reactive functional modification of the hydroxy group and the subsequent replacement thereof by hydroxy with the configuration being reversed. For that purpose, the amino and hydroxy groups shown in formula (I) are bridged by a bivalent group, especially carbonyl, there being obtained a compound of formula (IX):

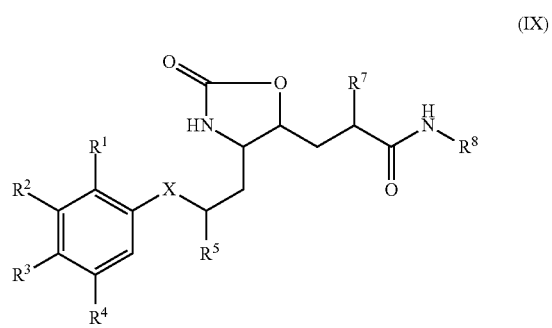

(IX)

which can be cleaved again by treatment with thionyl chloride with the configuration being reversed.

The ring-opening process of the invention can be carried out on a batch or continuous basis and, if desired, with recycle of recovered catalyst and/or other component(s) of the reaction medium.

As a result of the close relationship between the compounds herein in free form and in the form of their salts, hereinabove and hereinbelow any reference to the free compounds and their salts is to be understood as including also the corresponding salts and free compounds, respectively, as appropriate and expedient.

The invention relates also to pharmaceutical compositions comprising compounds of formula (I).

The pharmacologically acceptable compounds of the present invention may be used, for example, in the preparation of pharmaceutical compositions that comprise an effective amount of the active ingredient together or in admixture with a significant amount of inorganic or organic, solid or liquid, pharmaceutically acceptable carriers.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

The pharmaceutical compositions of the present invention are prepared in a manner known per se, for example by means of conventional dissolving, lyophilising, mixing, granulating or confectioning processes.

In one non-limiting embodiment herein the pharmaceutical compositions comprising compounds of formula (I) can be employed for treatment of hypertension and glaucoma. In one non-limiting embodiment herein t-boc is understood to be within $X^1$ and/or Act.

Examples 1-32

An improved method for the preparation of aliskiren from advanced lactone 1,1-dimethylethyl[(1S,3S)-3-[[4-methoxy-3-(3-methoxypropoxy)phenyl]methyl]-4-methyl-1-[(2S,4S)-tetrahydro-4-(1-methylethyl)-5-oxo-2-furanyl]pentyl]carbamate is described below.

The new method replaces a nucleophilic catalyst with a less expensive acid monocarboxylic catalyst in the first step and replaces gaseous HCl with aqueous HCl in the deprotection second step. Both new procedures demonstrate a significant reduction in time over the current procedure for making aliskiren.

The lactone, supra, is placed in a flask with 3-amino-2,2-dimethylpropanamide (3-20 equivalents). Acid catalyst 2-ethylhexanoic acid or cyclohexylcarboxylic acid (0.5-1 equivalent) is added and the reaction mixture is heated (40 minutes to 3 hours) at high temperature (100-140° C.). Under these conditions the reaction proceeds to between 78 and 93% conversion to give the desired amide. At temperatures between 100° C. and 125° C. no side products exceeding 5% are observed. The reaction mixture is partitioned between isopropyl acetate or ethyl acetate and water and the layers are separated. The product is then crystallized from the organic phase. The reaction does not proceed to any appreciable extent in ethanol at room temperature. Lower conversions are observed using tetrahydrofuran, toluene, ethanol, dimethylformamide, dichloromethane and isopropyl acetate/ethanol, tent-butyl acetate/ethanol, tetrahydrofuran/toluene and ethanol/toluene mixtures.

The amide is suspended in ethyl acetate and concentrated hydrochloric acid (12 equivalents) is added. After five minutes the reaction proceeds in greater than 98% conversion. The excess acid is quenched with aqueous NaOH and the product is extracted with either isopropyl acetate or ethyl acetate. The same result can be obtained by adding the amide directly to 10-12 molar hydrochloric acid (8-12 equivalents). After 2- to 15 minutes the reaction proceeds in greater than 98% conversion. Under both conditions no side-products exceeding 5% are observed.

The new method reduces the reaction times of both of the steps by approximately a factor of 50. The new route uses a smaller amount of a much less expensive catalyst for the first transformation and eliminates the use of a corrosive gas in the second step.

One equivalent of lactone was placed in a flask with the acid catalyst (monocarboxylic acid catalyst) and the amine. The indicated solvent was added and the flask was sealed and heated to the indicated temperature for the indicated time. The product and recovered starting material were isolated following column chromatography.

Table 1, below, sets forth the results of conducting a series of ring opening reactions separately employing the solvent tetrahydrofuran (THF), dimethylformamide (DMF), dichloromethane ($CH_2Cl_2$), ethanol (EtOH), iso-propyl acetate (iPrOAc) and tert-butyl acetate (tBuOAc). The reactions were heated at the indicated temperature for the indicated time.

The reactions were run using one equivalent of lactone which was placed in a flask with the noted equivalents of acid catalyst (monocarboxylic acid catalyst) and the noted equivalents of amine. The amine is 3-amino-2,2-dimethylpropionamide and the acid is 2-ethylhexanoic acid. The lactone is 1,1-dimethylethyl[(1S,3S)-3-[[4-methoxy-3-(3-methoxypropoxy)phenyl]methyl]-4-methyl-1-[(2S,4S)-tetrahydro-4-(1-methylethyl)-5-oxo-2-furanyl]pentyl]carbamate. The reactions were heated at the indicated temperature for the indicated time. Yields are based on the limiting reagent which for all lactone ring-opening reactions is the lactone. In some cases the desired product was contaminated with a byproduct and yields will exceed 100%. The amount of recovered lactone is also indicated. The % product, determined by HPLC, for all reactions herein is based on the limiting reagent, i.e., the lactone or the Boc-protected amine, depending on the particular reaction.

TABLE 1

Initial Solvent Screens Using 2-Ethylhexanoic Acid (Isolated Yields)

| Example | Solvent | Equiv. Acid | Equiv. Amine | t (h) | T (° C.) | Additive | % Product | % Lactone |
|---|---|---|---|---|---|---|---|---|
| 1 | THF | 0.5 | 3 | 6 | 100 | none | 66 | 20 |
| 2 | THF | 1 | 3 | 6 | 100 | none | 68 | 30 |
| 3 | THF | 2 | 3 | 6 | 100 | none | 66 | |
| 4 | THF | 3 | 3 | 6 | 100 | none | 56 | 47 |
| 5 | THF | 5 | 3 | 6 | 100 | none | 53 | |
| 6 | THF | 1 | 3 | 6 | 115 | none | 68 | 33 |
| 7 | THF | 1 | 3 | 6 | 130 | none | 53 | 44 |
| 8 | THF | 1 | 5 | 6 | 100 | none | 82 | 17 |
| 9 | THF | 1 | 7 | 6 | 100 | none | 93 | 10 |
| 10 | THF | 1 | 3 | 6 | 100 | none | 73 | 30 |
| 11 | DMF | 1 | 3 | 6 | 100 | none | 48 | 45 |
| 12 | $CH_2Cl_2$ | 1 | 3 | 6 | 100 | none | 58 | 42 |
| 13 | toluene | 1 | 3 | 6 | 100 | none | 63 | 38 |
| 14 | $CH_2Cl_2$:$H_2O$ | 1 | 3 | 6 | 100 | none | 5 | 87 |
| 15 | EtOH | 1 | 3 | 6 | 100 | none | 74 | 24 |
| 16 | THF | 1 | 3 | 6 | 100 | 2-OH-py | 72 | 28 |
| 17 | THF | 1 | 3 | 1 | 100 | none | 57 | 57 |
| 18 | THF | 1 | 3 | 2 | 100 | none | 69 | 40 |
| 19 | THF | 1 | 3 | 4 | 100 | none | 72 | 27 |
| 20 | EtOH | 1 | 3 | 1 | 100 | none | 14 | 76 |
| 21 | EtOH | 1 | 3 | 18 | rt | none | <10* | 90-95 |
| 22 | EtOH/THF** | 1 | 3 | 2 | 100 | none | 34 | 65 |
| 23 | THF | 0 | 3 | 2 | 100 | none | 4 | 95 |
| 24 | THF | 1*** | 3 | 2 | 100 | none | 67 | 30 |
| 25 | EtOH/THF**** | 1 | 3 | 2 | 100 | none | 53 | 48 |

TABLE 1-continued

Initial Solvent Screens Using 2-Ethylhexanoic Acid (Isolated Yields)

| Example | Solvent | Equiv. Acid | Equiv. Amine | t (h) | T (° C.) | Additive | % Product | % Lactone |
|---|---|---|---|---|---|---|---|---|
| 26 | EtOH/THF**** | 1 | 3 | 4 | 100 | none | 68 | 28 |
| 27 | EtOH/THF**** | 1 | 3 | 6 | 100 | none | 57 | 21 |
| 28 | iPrOAc/EtOH**** | 1 | 3 | 4 | 100 | none | 59 | 30 |
| 29 | tBuOAc/EtOH**** | 1 | 3 | 4 | 100 | none | 64 | 29 |
| 30 | THF | 1 | 3 | 4 | 100 | iPr$_2$EtN | 67 | 32 |
| 31 | THF | 1 | 3 | 4 | 100 | Et3N | 48 | 28 |
| 32 | THF | 1 | 4 | 4 | 100 | none | 19 | 73 |

*based on thin layer chromatography
**0.10 mL with 25 mg lactone
***cyclohexyl carboxylic acid
****1:1
h = hours
Equiv. = equivalents
T = temperture
2-OH—py = 2-hydroxypyridine
rt = room temperature

Examples 33-58

For the reactions summarized in Table 2 below, 50 mg of the lactone was placed in a vial and a 1 M solution of amine, i.e., 3-amino-2,2-dimethylpropionamide, in the indicated solvent was added or the amine was added as a solid followed by the indicated solvent (0.05 mL) followed by 1 equiv. of 2-ethylhexanoic acid. Some water is 2-3 drops. Conversions were measured by HPLC.

TABLE 2

Solvent Screening Cont.

| Example | Equiv. Amine | T (° C.) | Time (h) | % Product | % Lactone | Solvent |
|---|---|---|---|---|---|---|
| 33 | 5.37 | 120 | 1 | 54 | 45 | THF some H2O |
| 34 | 5.37 | 120 | 2 | 31 | 69 | THF some H2O |
| 35 | 5.37 | 120 | 3 | 85 | 15 | THF some H2O |
| 36 | 5.37 | 120 | 1 | 16 | 83 | THF some H2O |
| 37 | 5.37 | 120 | 2 | 28 | 72 | THF some H2O |
| 38 | 5.37 | 120 | 2.5 | 29 | 71 | THF some H2O |
| 39 | 5.37 | 120 | 1 | 16 | 83 | 2-Me-THF |
| 40 | 5.37 | 120 | 2 | 33 | 67 | 2-Me-THF |
| 41 | 5.37 | 120 | 2.5 | 36 | 64 | 2-Me-THF |
| 42 | 5.37 | 120 | 1 | NA | | 4:1 H2O/THF |
| 43 | 5.37 | 120 | 2 | NA | | 4:1 H2O/THF |
| 44 | 5.37 | 120 | 2.5 | NA | | 4:1 H2O/THF |
| 45 | 5.37 | 120 | 1 | 45 | 55 | Tolune/EtOH |
| 46 | 5.37 | 120 | 2 | 63 | 37 | |
| 47 | 5.37 | 120 | 3 | 68 | 32 | |
| 48 | 5.37 | 120 | 4 | 58 | ? | |
| 49 | 5.37 | 120 | 1 | 63 | 37 | THF |
| 50 | 5.37 | 120 | 2 | 80 | 20 | |
| 51 | 5.37 | 120 | 3 | 84 | 26 | |
| 52 | 5.37 | 120 | 4 | 80 | 20 | |
| 53 | 5.37 | 120 | 1 | 60 | 40 | toluene |
| 54 | 5.37 | 120 | 2 | 58 | 42 | |
| 55 | 5.37 | 120 | 3 | 60 | 40 | |
| 56 | 5.37 | 120 | 4 | 57 | 43 | |
| 57 | 5.37 | 120 | 2.5 | 70 | 30 | THF (200 ul) |
| 58 | 5.37 | 120 | 2.5 | 74 | 25 | 2-Me-THF (200 uL) |

Examples 59-67

For the reactions whose results are set forth in Table 3 below, 50 mg of the lactone of the previous examples was placed in a flask with the amine, 3-amino-2,2-dimethylpropionamide, the indicated amount of the indicated solvent and 1 equiv. of 2-ethylhexanoic acid. Equivalents as used herein is understood to be based on the equivalents of lactone unless expressed otherwise.

TABLE 3

Solvent Screens, Cont. (Conversions Measured by HPLC)

| Example | Equiv. Amine | T (° C.) | Time (h) | % Product | % Lactone | Solvent | mL Solvent |
|---|---|---|---|---|---|---|---|
| 59 | 3 | 120 | 2 | 60 | 40 | toluene | 0.19 |
| 60 | 5 | 120 | 2 | 59 | 41 | toluene | 0.25 |
| 61 | 7 | 120 | 2 | 63 | 36 | toluene | 0.31 |
| 62 | 3 | 120 | 2 | 33 | 66 | EtOAc | 0.19 |
| 63 | 5 | 120 | 2 | 10 | 89 | EtOAc | 0.25 |
| 64 | 7 | 120 | 2 | 57 | 42 | EtOAc | 0.31 |
| 65 | 3 | 120 | 2 | 69 | 30 | THF | 0.19 |
| 66 | 5 | 120 | 2 | 80 | 19 | THF | 0.25 |
| 67 | 7 | 120 | 2 | 87 | 13 | THF | 0.31 |

Examples 68-72

In these examples, 1 equiv. of lactone of the previous examples, and in separate reactions, 3, 5, 7.5, 10 and 20 equiv. of the amine 3-amino-2,2-dimethylpropionamide, were heated to 120° C. with 1 equiv. of the acid catalyst. The conversions, measured by HPLC, are reported in FIG. 1 (Graph 1: Lactone Opening with No Solvent 120° C.).

Examples 73-75

Figure 2:
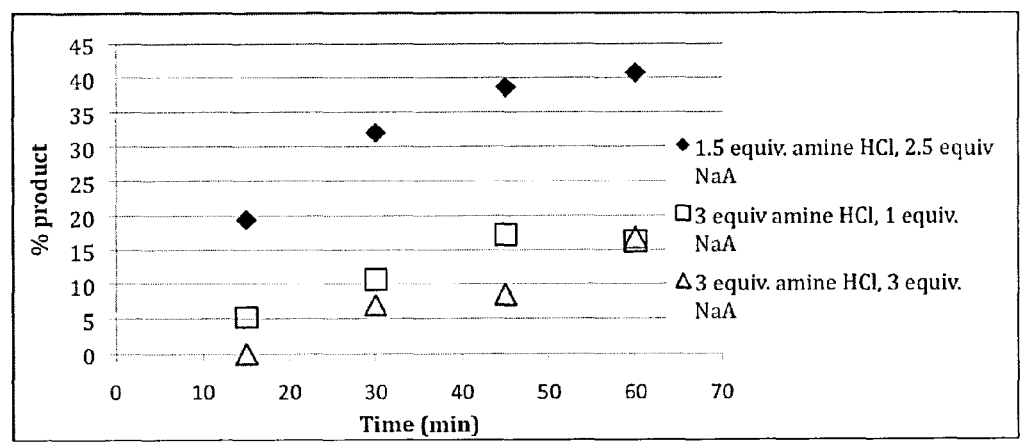

Employing substantially the same procedures as in Examples 68-72, supra, the sodium carboxylate of 2-ethylhexanoic acid (NA) was substituted for the acid catalyst in said examples and the ammonium chloride salt of 3-amino-2,2-dimethylpropeonamide (amide HCl) was substituted for free amine. 100 mg lactone was employed. The results of these reactions, employing the amounts of amine HCl and NA indicated in FIG. 2 (Graph 2: Lactone Opening with No Solvent at 120° C.), are reported therein.

Examples 76-78

Figure 3:
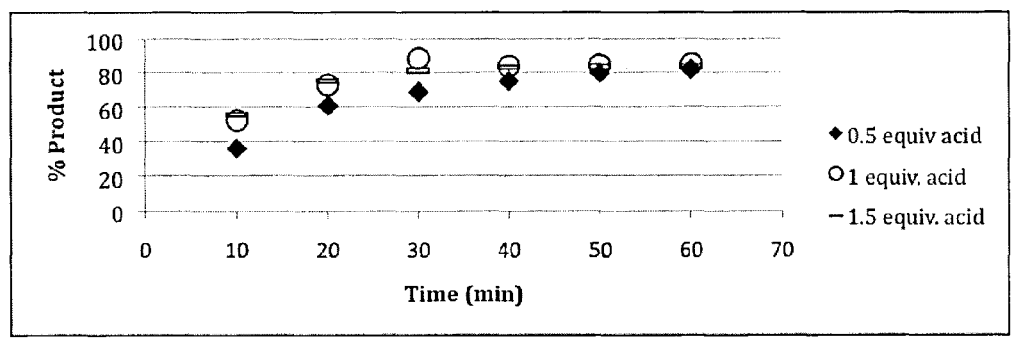

In these examples, 100 mg of the lactone of the previous examples were separately reacted with 5 equivalents of 3-amino-2,2-propionamide heated to 120° C. employing 0.5, 1.0 or 1.5 equivalents of 2-ethylhexanoic acid with the results shown in FIG. 3 (Graph 3: Varying Equiv. of 2-Ethylhexanoic Acid).

Examples 79-82

Figure 4:
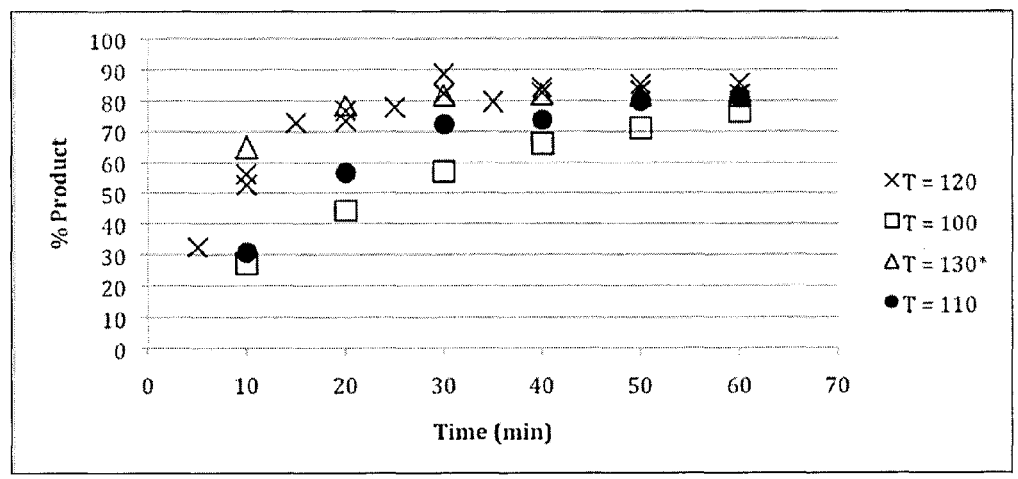

These examples illustrate the effect of varying the temperature of a series of reactions employing 5 equiv. 3-amino-2,2-dimethylpropionamide, 100 mg lactone and 2-ethylhexanoic acid. The reaction temperatures are 120, 100, 130 and 100° C. The results of the reactions as determined by HPLC are reported in FIG. 4 (Graph 4: Effect of Temperature on the Lactone Opening Reaction).

Examples 83-86

Figure 5:
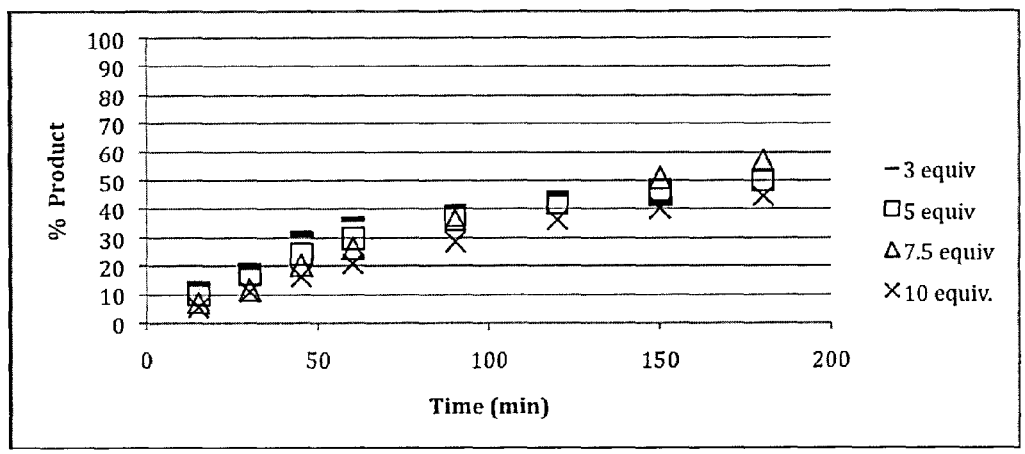

These examples illustrate the effect of using solvent and varying amounts of amine for the lactone opening reaction. For the reactions, 3-amino-2,2-dimethylpropionamide dissolved in ethanol (2 molar) and lactone dissolved in toluene (0.5 molar, 0.40 ml) were heated to 120° C. The amine was added in amounts of 3, 5, 7.5 and 10 equivalents. One equivalent of 2-ethylhexanoic acid was used. The results of the reactions, monitored by HPLC, are reported in FIG. 5 (Graph 5: Effect of Solvent on the Lactone Opening Reaction).

Examples 87-95

These examples illustrate the deprotection of the ring-opened lactone having its amine function protected by tert-butyoxycarbonyl group (Boc) to provide aliskiren as described above.

Figure 6:
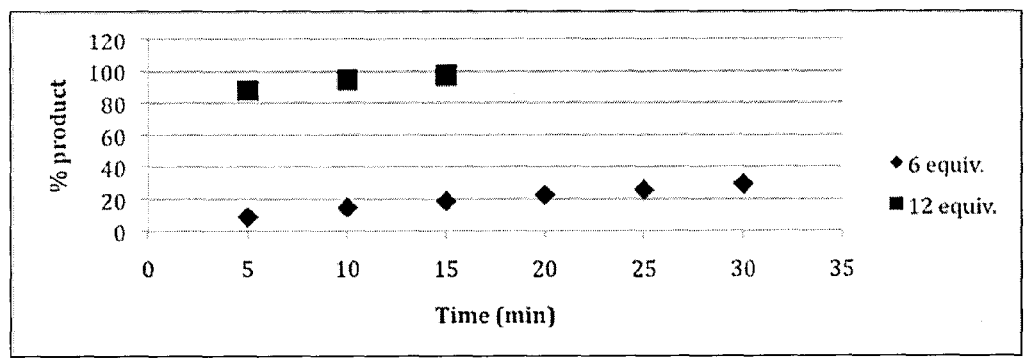

For the deprotection reactions whose results are reported in FIG. 6 (Graph 6: Removal of the tert-butyoxycarbonyl group (Boc)), 100 mg of the protected ring-opened lactone was suspended in 0.45 ml ethyl acetate and concentrated HCL, 6 or 12 equiv., was added. The percentage of deprotected product at various time intervals was determined by HPLC.

Examples 96-106

Deprotection reactions were carried out upon solid ring-opened Boc-protected amine (100 mg) in a flask using varying amounts of aqueous HCl followed by quenching with aqueous NaOH diluted with ethanol at the end of 2 or 3 minutes. The percentage of deprotected product was measured by HPLC.

Figure 7:
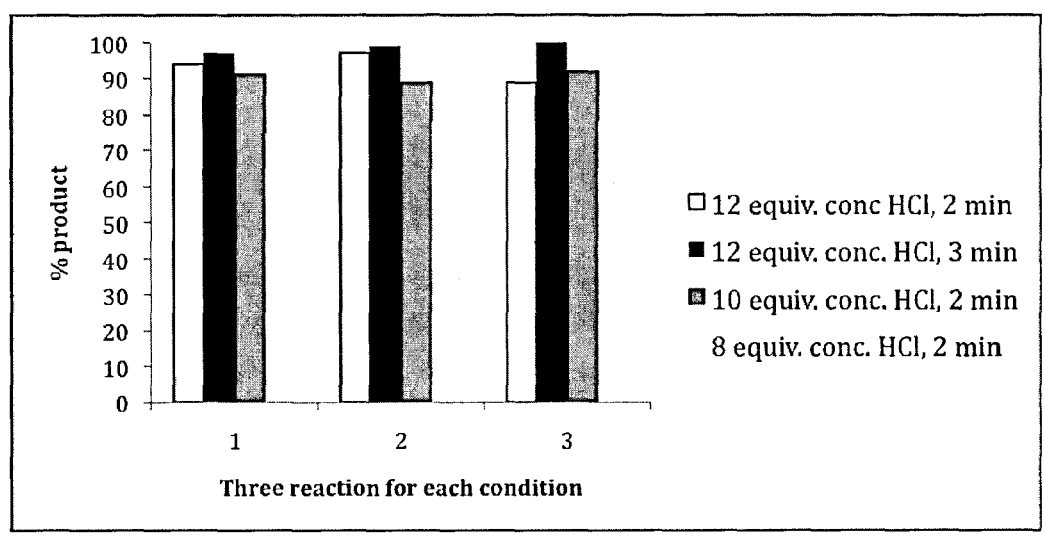
Figure 8:
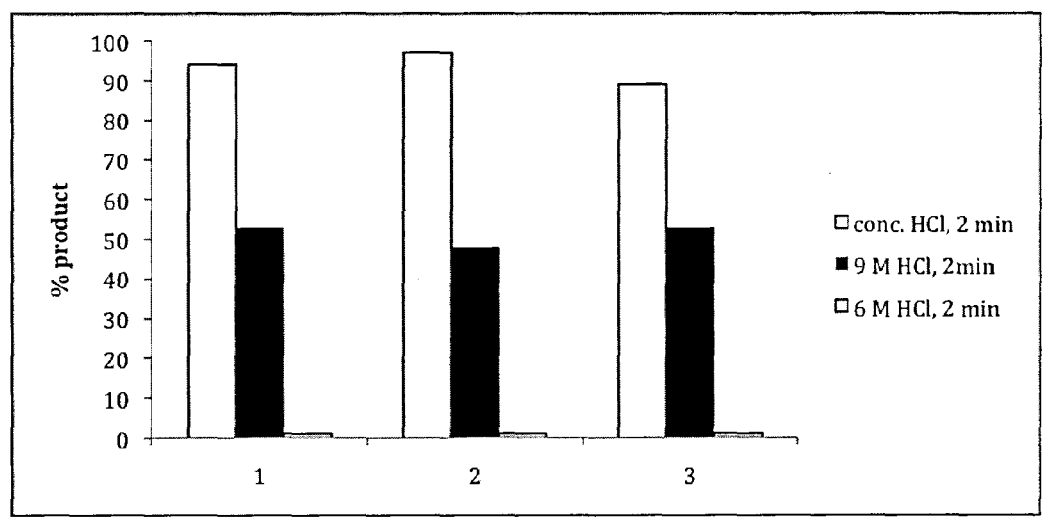

FIGS. 7 and 8 set forth in bar graph form the deprotection results obtained with 12 equiv. conc. HCl at 2 min. (Example 96), 12 equiv. conc. HCl at 3 minutes (Example 97), 10 equiv. conc. HCl at 2 min. (Example 98), 2 equiv. conc. HCl at 2 minutes (Example 99), 12 M conc. HCl at 2 minutes (Example 100), 9 M HCl at 2 minutes (Examples 101) and 6 M HCl at 2 minutes (Example 102).

Figure 9:
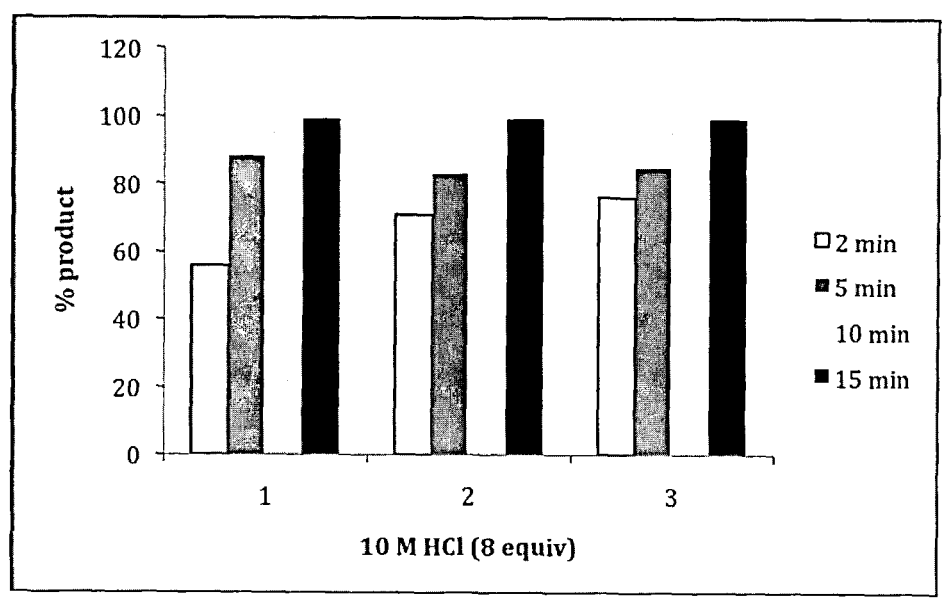

FIG. 9 sets forth the deprotection results obtained with 10 M HCl for reaction periods of 2, 5, 10 and 15 minutes (Examples 103-106) as determined by HPLC.

Examples 107-164

These examples illustrate the preparation of lactone ring-opened Boc-protected amide (3) (Example 107) under varying conditions of reaction temperature and amine equivalents (Examples 108-126: results set forth below in Table 4); using different aliphatic carboxylic acids (Examples 127-142: results set forth below in Table 5); using different amines (Examples 143-147: results set forth in Table 5); and, using benzoic acid and various substituted benzoic acid catalysts (Examples 161-177: results set forth in Table 7).

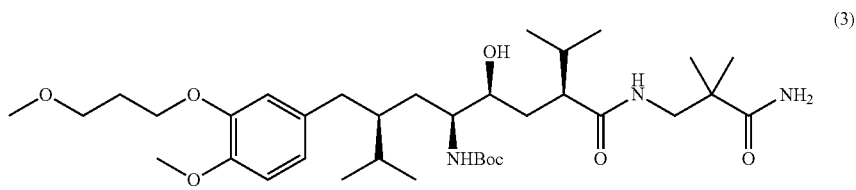 [SMILES: COCCCOc1cc(C[C@@H](C[C@H](NC(=O)OC(C)(C)C)[C@@H](O)C[C@H](C(=O)NCC(C)(C)C(N)=O)C(C)C)C(C)C)ccc1OC]

(3)

Preparation of amide (3): A 20 mL microwave vial equipped with a stir bar was charged with lactone(2) (1.00 g, 1.87 mmol):

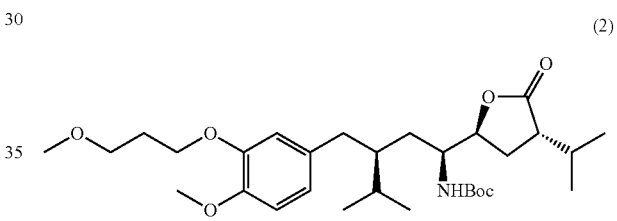

(2)

amine (4) (1.08 g, 9.33 mmol):

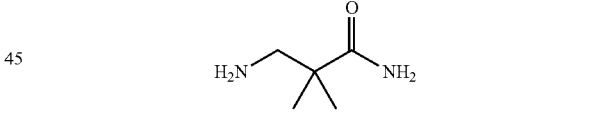

(4)

and 2-ethylhexanoic acid (0.30 mL, 1.88 mmol). The vial was placed in an oil bath at 120° C. and the reaction stirred for 50 minutes. The vial was removed from the oil bath and EtOAc (5 mL) and water (5 mL) were added immediately. The solution was stirred and allowed to cool to room temperature before being poured into a separatory funnel. The layers were separated and the aqueous phase was extracted twice with EtOAc. The combined organic extracts were washed with brine, dried over $M_gSO_4$ and concentrated to give a white solid. Following flash chromatography (1:1 hexanes:EtOAc to 9:1 CH3Cl2:MeOH), amide (3) was isolated in 84% yield (1.03 g, 1.57 mmol), 15% of the starting lactone was recovered (159 mg, 0.29 mmol).

Heating amide (3) to 120° C. in the presence of one equivalent of 2-ethylhexanoic acid afforded a 40:60 ratio of lactone (2) to amide 3 after 30 minutes. The ratio remained the same after and additional 60 minutes of heating. Heating amide (3) to 120° C. in the presence of 4 equivalents of amine (4) (the approximate amount remaining after 50 minutes of the forward reaction) and one equivalent of 2-ethylhexanoic acid gave an 85:15 ratio of 3:2 after 30 minutes, the ratio did not change upon extended heating. This is the same product ratio observed when starting with 1 equivalent of lactone (2) and 5 equivalents of amine (4) in the presence of one equivalent of ethylhexanoic acid.

The series of reactions whose results are set forth in Table 4 below were run using 1 equiv. of lactone (2) (250 mg, 0.47 mmol) and 1 equivalent of 2-ethylhexanoic acid. Byproduct formation was observed after 30 minutes. When the reaction was heated to 140° C., byproduct formation was significant.

TABLE 4

Effect of Temperature and Amine Equivalents

| Example | T (° C.) | Equiv. amine (4) | Time (min) | Conversion |
|---|---|---|---|---|
| 108 | 100 | 5 | 50 | 71 |
| 109 | 110 | 5 | 50 | 80 |
| 110 | 120 | 5 | 50 | 84 |
| 111 | 120 | 5 | 120 | 83 |
| 112 | 130 | 5 | 50 | 80 |
| 113 | 120 | 3 | 50 | 75 |
| 114 | 120 | 3 | 120 | 78 |
| 115 | 120 | 6 | 50 | 87 |
| 116 | 120 | 7 | 50 | 88 |
| 117 | 120 | 8 | 50 | 89 |
| 118 | 120 | 9 | 50 | 90 |
| 119 | 120 | 10 | 50 | 89 |
| 120 | 120 | 10 | 120 | 88 |
| 121 | 120 | 15 | 50 | 90 |
| 122 | 120 | 20 | 50 | 83 |
| 123 | 120 | 20 | 120 | 93 |
| 124 | 120 | 100 | 50 | 64 |
| 125 | 120 | 100 | 120 | 86 |
| 126 | 120 | 100 | 240 | 94 |

The series of reactions whose results are set forth in Table 5 below were run using 1 equiv. of lactone (2) (250 mg, 0.47 mmol), 5 equiv. of amine (4) (271 mg, 2.33 mmol) and 1 equiv. of the indicated acid at 120 (° C.) for 50 minutes.

TABLE 5

Screen of Aliphatic Carboxylic Acids

| Example | Acid | Product Appearance | Conversion |
|---|---|---|---|
| 127 | acetic | visible solid | 75 |
| 128 | propanoic | homogeneous | 83 |
| 129 | butyric | homogeneous | 82 |
| 130 | pentanoic | homogeneous | 84 |
| 131 | hexanoic | homogeneous | 82 |
| 132 | octanoic | homogeneous | 82 |
| 133 | pivalic | homogeneous | 85 |
| 134 | cyclopentanoic | homogeneous | 82 |
| 135 | cyclohexanoic | homogeneous | 85 |
| 136 | trichloroacetic | visible solid | 51 |
| 137 | perflurooctanoic | visible solid | 35 |
| 138 | camphoric | visible solid | 66 |
| 139 | camphoric | visible solid | 84 (3 h) |
| 140 | fumaric | visible solid | 17 |
| 141 | malic | visible solid | 10 |
| 142 | tartaric | visible solid | 7 |

The series of reactions whose results are set forth in Table 6 were conducted under substantially the same conditions as in Example 107 at 83° C. with the indicated amines. The yields (%) of amide product were determined by HPLC.

TABLE 6

Effect of Different Amines on Yield of Amine

| Example | Amine | Yeld (%) of Amide Product |
|---|---|---|
| 143 | amine (4) | 83 |
| 144 | hexylamine | 82 |
| 145 | benzylamine | 79 |
| 146 | neopentyl amine | 76 |
| 147 | cyclohexyl amine | 60 |

The series of reactions whose results are set forth in Table 7 were conducted with lactone (2) (250 mg, 0.47 mmol) amine 4 (271 mg, 2.33 mmol) and one equiv. of benzoic acid or substituted benzoic acid heated for 120° C. for 50 min. All conversions were determined by HPLC.

TABLE 7

Effect of Benzoic Acid Substitution on Reaction Rate

| Example | Benzoic Acid Substituent | pK$_2$ (in DMSO) | α | Relative Rate (rat$_x$/rate$_H$) | Conversion at 50 min (%) |
|---|---|---|---|---|---|
| 148 | 3-(CH$_3$)$_2$N$^c$ | 5.1 | −.211 | 1.16$^b$ | 70$^b$ |
| 149 | 3-Me | 4.24 | −.069 | 1.14$^b$ | 71$^b$ |
| 150 | H | 4.2 | 0 | 1 | 69$^b$ |
| 151 | 2-OMe | 4.09 | | 0.74 | 59$^b$ |
| 152 | 3-OMe | 4.09 | .115 | 0.94$^b$ | 68$^b$ |
| 153 | 2-Me | 3.91 | | 1.12 | 72$^b$ |
| 154 | 3-I | 3.86 | .352 | 0.69$^b$ | 53$^b$ |
| 155 | 3-Cl | 3.83 | .373 | 0.65$^b$ | 55$^b$ |
| 156 | 3-Br | 3.81 | .391 | 0.60$^b$ | 54$^b$ |
| 157 | 3-CF$_3$ | 3.79 | .46 | 0.61$^b$ | 51$^b$ |
| 158 | 3-NO$_2$ | 3.45 | .71 | 0.53$^b$ | 49$^b$ |
| 159 | 4-NO$_2$ | 3.44 | .778 | 0.45 | 42$^b$ |
| 160 | 2-Cl | 2.94 | | 0.49 | 45 |
| 161 | 2-Br | 2.85 | | 0.51 | 42 |
| 162 | 2-I | 2.85 | | 0.47 | 44 |
| 163 | nicotinic | 2.84 | | | 46 |
| 164 | picolinic | 1.07 | | 0.27 | 27 |

Examples 165-190

These examples illustrate the effect of various acid catalysts both within and outside the scope of the invention on the reaction of lactone (2) with amine (4) to provide amide (3). In the series of reactions whose results are set forth in Table 8, 1 equiv. lactone (2) was placed in a flask with 5 equiv. amine (4). The indicated acid catalyze was then added and the reaction mixtured heated for 45 min. at 20° C. The conversion (%) to amide (3) was determined by HPLC.

TABLE 9

Screen of Aliphatic Carboxylic Acids

| Example | Acid Catalyst | Conversion (%) | Appearance of Reaction Mixture |
|---|---|---|---|
| 165 | fumaric acid | 17.0 | very cloudy |
| 166 | tiglic acid | 85.0 | homogeneous |
| 167 | valeric | 83.6 | homogeneous |
| 168 | 2-ethylhexanoic acid | 85.0 | homogeneous |
| 169 | 5-hexenoic acid | 82.5 | homogeneous |
| 170 | acetic acid | 75.5 | some solid crashed out |
| 171 | butyric acid | 82.2 | some foam formed |
| 172 | cyclohexanecarboxylic acid | 84.9 | homogeneous |
| 173 | pivalic acid | 84.7 | homogeneous |
| 174 | propionic acid | 82.5 | homogeneous |
| 175 | tartaric acid | 8.9 | very cloudy |

TABLE 9-continued

Screen of Aliphatic Carboxylic Acids

| Example | Acid Catalyst | Conversion (%) | Appearance of Reaction Mixture |
|---|---|---|---|
| 176 | malic acid | 9.7 | slightly cloudy |
| 177 | benzoic acid | 70.5 | homogeneous |
| 178 | o-anisoic acid | 61.3 | homogeneous |
| 179 | p-trifluoromethylbenzoic acid | 48.6 | cloudy |
| 180 | p-nitrobenzoic acid | 43.4 | cloudy |
| 181 | boronic acid | 9.2 | homogeneous |
| 182 | trichloroacetic acid | 21.0 | very cloudy |
| 183 | Er(Otf)$_3$ | 21.0 | very cloudy |
| 184 | Yb(Otf)$_3$ | 21.0 | very cloudy |
| 185 | LiBr | 7.3 | homogeneous |
| 186 | LiCl | 8.6 | homogeneous |
| 187 | sulfuric acid | 13.3 | precipitate |
| 188 | phosphoric acid | 10.7 | precipitate |
| 189 | hydrochloric acid | 5.5 | homogeneous |
| 190 | p-toluenesulfonic acid | 32.5 | homogeneous |

While the above description comprises many specifics, these specifics should not be construed as limitations, but merely as exemplifications of specific embodiments thereof. Those skilled in the art will envision many other embodiments within the scope and spirit of the description as defined by the claims appended hereto.

The invention claimed is:

1. A process of opening the ring of a ring-containing compound which comprises reacting a ring-containing compound possessing at least one lactone ring with at least one amine in the presence of at least one monocarboxylic acid in the amount of from 0.5 equivalents to 1.5 equivalents to the molar amount of said ring-containing compound, without the presence of a metal salt catalyst, and under conditions sufficient to open the at least one ring and provide ring-opened reaction product, wherein the ring containing compound possessing the at least one lactone ring is selected from the group consisting of γ-decanolactone, β-butyrolactone, δ-decanolactone, β-propiolactone, D-glucono-δ-lactone, ε-caprolactone, δ-caprolactone, γ-butyrolactone, γ-caprolactone, 4R,4aS,7R,7aR)-4-((R)-2,2-dimethyl-1,3-dioxolan-4-yl)-7-methoxy-2,2-dimethyldihydro-4H-furo[3,2-d][1,3]dioxin-6(4aH)-one, (3aR,6R,6aR)-6-((tert-butyldimethylsilyloxy)methyl)-2,2-dimethyldihydrofuro[3,4-d][1,3]-dioxol-4(3aH)-one, (3aR,4S,5R,6aS)-4-((tert-butyldimethylsilyloxy)methyl)-5-((tetrahydro-2H-pyran-2-yloxy)methyl)hexahydro-2H-cyclopenta[b]furan-2-one, and 1,1-dimethylethyl[(1S,3S)-3-[[4-methoxy-3-(3-methoxypropoxy)phenyl]methyl]-4-methyl-1-[(2S,4S)-tetrahydro-4-(1-methylethyl)-5-oxo-2-furanyl]pentyl]carbamate wherein the at least one amine is of the formula H$_2$N—R wherein R is lower alkyl, cycloalkyl, free or aliphatically esterified or etherified hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N- di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, or the group —CH$_2$C(CH$_3$)C(=O)NH$_2$ or a salt thereof; and wherein the at least one monocarboxylic acid is of the general formula RCOOH wherein R is alkyl, cycloalkyl, alkenyl, aryl, substituted aryl or aralkyl of up to 30 carbon atoms, optionally substituted with at least one halogen atom.

2. The process of claim 1 wherein the ring-containing compound and/or ring-opened reaction product possesses at least one protecting group.

3. The process of claim 1 wherein the ring-containing compound is at least one member of the group consisting of general formula (A):

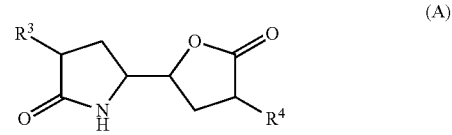

(A)

wherein

R$^3$ is C$_{1-7}$ alkyl or C$_{3-8}$ cycloalkyl; and R$^4$ is C$_{1-7}$ alkyl, C$_{2-7}$ alkenyl, C$_{3-8}$ cycloalkyl, phenyl- or naphthyl-C$_{1-4}$ alkyl each unsubstituted or mono-, di- or tri-substituted by C$_{1-4}$ alkyl, O—C$_{1-4}$ alkyl, OH, C$_{1-4}$ alkylamino, di-C$_{1-4}$ alkylamino, halogen and/or by trifluoromethyl; or a salt thereof, and general formula (B):

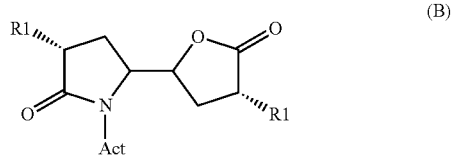

(B)

wherein each R$^1$ is independently of one another hydrogen; C$_{1-7}$ alkyl, C$_{3-8}$ cycloalkyl or benzyl, in particular both R$^1$ are branched C$_{3-6}$ alkyl such as isopropyl; and, Act is an activating group selected from an amino protecting group; or a salt thereof.

4. The process of claim 1 for making δ-Amino-γ-hydroxy-ω-aryl-alkanoic acid amide of the general formula (I):

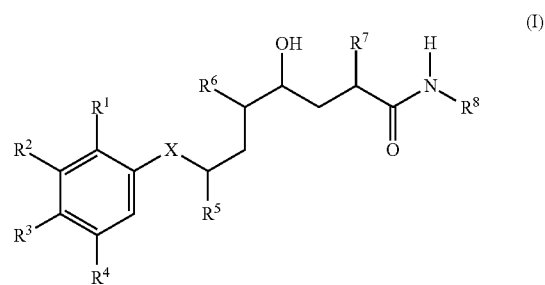

(I)

wherein $R^1$ is hydrogen, hydroxy, lower alkoxy, cycloalkoxy, lower alkoxy-lower alkoxy or free or esterified or amidated carboxy-lower alkoxy, $R^2$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, optionally hydrogenated heteroaryl-lower alkoxy, cyano-lower alkoxy, free or esterified or amidated carboxy-lower alkoxy or free or esterified or amidated carboxy-lower alkyl, $R^3$ is optionally halogenated lower alkyl, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene; cyano-lower alkoxy or free or esterified or amidated carboxy lower alkoxy, or together with R.sub.4 is lower alkylenedioxy or a fused-on benzo or cyclohexeno ring, $R^4$ together with $R^3$ is lower alkylenedioxy or a fused-on benzo or cyclohexeno ring, or is hydrogen, lower alkyl, hydroxy, lower alkoxy or cycloalkoxy, X is methylene or hydroxymethylene, $R^5$ is lower alkyl or cycloalkyl, $R^6$ is unsubstituted or N-mono- or N,N-di-lower alkylated or N-lower alkanoylated amino, $R^7$ is hydrogen, lower alkyl, lower alkenyl, cycloalkyl or aryl-lower alkyl, and $R^8$ is lower alkyl, cycloalkyl, free or aliphatically esterified or etherified hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterideal or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, and to the salts thereof, comprising:

performing the process of claim 1 on an intermediate compound which is a precursor to said δ-amino-γ-hydroxy-ω-aryl-alkanoic acid amide.

5. The process of claim 4 wherein the δ-amino-γ-hydroxy-ω-aryl-alkanoic acid is an amide selected from the group consisting of amides of formula (II):

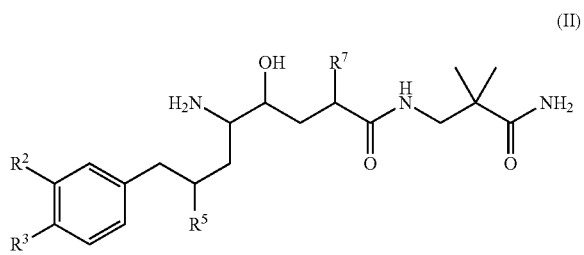

(II)

wherein $R^7$ is hydrogen, $C_{1-7}$ alkyl, $C_{3-8}$ cycloalkyl or benzyl, $R^2$ is halogen, hydroxyl, $C_{1-6}$ halogenalkyl, $C_{1-6}$ alkoxy-$C_{1-6}$ alkyloxy or $C_{1-6}$ alkoxy-$C_{1-6}$ alkyl; $R^3$ is halogen, hydroxyl, $C_{1-4}$ alkyl or $C_{1-4}$ alkoxy, or salt thereof, amides of formula (III):

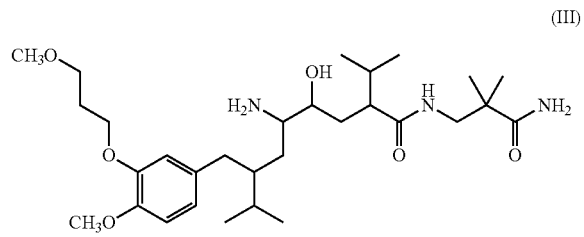

(III)

or salt thereof, amides of formula (IV):

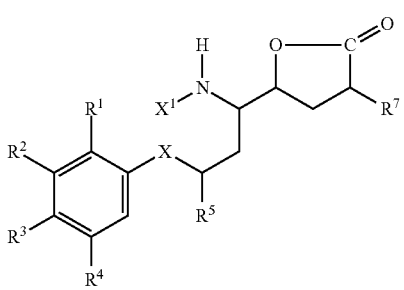

(IV)

wherein $R^1$, $R^2$, $R^3$, $R^4$, $R^5$, $R^7$, and X are as defined and $X^1$ is an amino-protecting group, and further, wherein the lactone of general formula (IV) is reacted with an amine of the general formula (V): $H_2N—R^8$, wherein $R^8$ is as defined,
and amides of general formula (VI):

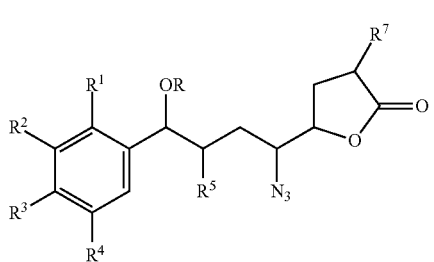

(VI)

wherein $R^1$, $R^2$, $R^3$, $R^4$, $R^5$ and $R^7$ are as defined and the group —OR is a free or esterified or etherified hydroxyl group with R being a hydroxyl protecting group, and further,
wherein the lactone of general formula (VI) is reacted with an amine of the general formula (V): $H_2N—R^8$, wherein $R^8$ is as defined.

6. The process of claim 1 for making a δ-amino-γ-hydroxy-ω-aryl-alkanoic acid amide of the general formula (I):

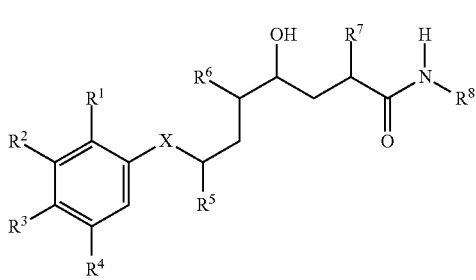

(I)

wherein $R^1$ is hydrogen, hydroxy, lower alkoxy, cycloalkoxy, carboxy-lower alkoxy or free, esterified or amidated carboxy-lower alkoxy,
$R^2$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, optionally hydrogenated heteroaryl-lower alkoxy, cyano-lower alkoxy, free or esterified or amidated carboxy-lower alkoxy or free or esterified or amidated carboxy-lower alkyl,
$R^3$ is optionally halogenated lower alkyl, lower alkoxy-lower alkyl, cycloalkoxy-lower alkyl, hydroxy-lower alkyl, optionally S-oxidised lower alkylthio-lower alkyl, optionally hydrogenareal heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene; cyano-lower alkoxy or free or esterified or amidated carboxy lower alkoxy, or together with $R^4$ is lower alkylenedioxy or a fused-on benzo or cyclohexeno ring,
$R^4$ together with $R^3$ is lower alkylenedioxy or a fused-on benzo or cyclohexeno ring, or is hydrogen, lower alkyl, hydroxy, lower alkoxy or cycloalkoxy,
X is methylene or hydroxymethylene,
$R^5$ is lower alkyl or cycloalkyl,
$R^6$ is unsubstituted or N-mono- or N,N-di-lower alkylated or N-lower alkanoylated amino,
$R^7$ is hydrogen, lower alkyl, lower alkenyl, cycloalkyl or aryl-lower alkyl, and
$R^8$ is lower alkyl, cycloalkyl, free or aliphatically esterified or etherified hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterideal or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, and to the salts thereof, comprising:

performing the process of claim 1 on an intermediate compound of said δ-amino-γ-hydroxy-ω-aryl-alkanoic acid amide; and, removing at least one protecting group on the intermediate compound and/or removing at least one protecting group on the ring-opened reaction product, with aqueous halogenic acid.

7. The process of claim 6 wherein a compound (2S,4S,5S,7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate is made by reacting 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl] carbamate with 3-amino-2,2-dimethylpropanamide in the presence of 2-ethylhexanoic acid or cyclohexanecarboxylic acid, or a mixture thereof to provide 2(S), 4(S), 5(S), 7(S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate, or, converting the reaction product to provide (2S,4S,5S,7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate.

8. The process of claim 7 wherein a compound (2S,4S,5S,7S)—N-(3-amino-2,2-dimethyl-3-oxopropyl)-2,7-di(1-methylethyl)-4-hydroxy-5-amino-8-[4-methoxy-3-(3-methoxypropoxy)phenyl]octanamide hemifumarate is made by reacting 1,1-dimethylethyl[(1S,3S)-3-[[4-methoxy-3-(3-methoxypropoxy)phenyl]methyl-4-methyl-1-[(2S,4S)-tetrahydro-4-(1-methylethyl)-5-oxo-2-furanyl]pentyl] carbamate with 3-amino-2,2-dimethylpropanamide in the presence of a catalyst other than monocarboxylic acid catalyst; and, removing at least one protecting group on the 1,1-dimethylethyl[(1S,3S)-3-[[4-methoxy-3-(3-methoxypropoxy)phenyl]methyl-3-4-methyl-1-[(2S,4S)-tetrahydro-4-(1-methylethyl)-5-oxo-2-furanyl]pentyl]carbamate and/or removing at least one protecting group on the reaction product with aqueous halogenic acid.

9. The process of claim 1 for preparing aliskiren.

* * * * *